United States Patent
Yang

(10) Patent No.: US 11,096,791 B2
(45) Date of Patent: Aug. 24, 2021

(54) ARTIFICIAL PROSTHESIS FOR KNEE ARTHROPLASTY

(71) Applicant: Chen Yang, Jilin (CN)

(72) Inventor: Chen Yang, Jilin (CN)

( * ) Notice: Subject to any disclaimer, the term of this patent is extended or adjusted under 35 U.S.C. 154(b) by 200 days.

(21) Appl. No.: 16/089,819

(22) PCT Filed: Mar. 28, 2017

(86) PCT No.: PCT/CN2017/078397
§ 371 (c)(1),
(2) Date: Sep. 28, 2018

(87) PCT Pub. No.: WO2017/167172
PCT Pub. Date: Oct. 5, 2017

(65) Prior Publication Data
US 2019/0117407 A1    Apr. 25, 2019

(30) Foreign Application Priority Data

Mar. 31, 2016  (CN) .......................... 201610196679.5
Mar. 31, 2016  (CN) .......................... 201610202287.5

(51) Int. Cl.
*A61F 2/38*    (2006.01)
*A61F 2/30*    (2006.01)

(52) U.S. Cl.
CPC ........ *A61F 2/3859* (2013.01); *A61F 2/30749* (2013.01); *A61F 2/38* (2013.01);
(Continued)

(58) Field of Classification Search
CPC .......... A61F 2/38; A61F 2/3859; A61F 2/389; A61F 2002/30125
See application file for complete search history.

(56) References Cited

U.S. PATENT DOCUMENTS 5,282,869 A      2/1994  Miyajima et al.
8,545,509 B2 *  10/2013  Park ..................... A61B 5/4533
                                                              606/88
(Continued)

FOREIGN PATENT DOCUMENTS

CN          2681706 Y      3/2005
CN        101361684 A      2/2009
(Continued)

OTHER PUBLICATIONS

"European Application Serial No. 17773202.1, Extended European Search Report dated May 12, 2020", (May 12, 2020), 12 pgs.
(Continued)

*Primary Examiner* — Brian A Dukert
(74) *Attorney, Agent, or Firm* — Schwegman Lundberg & Woessner, P.A.

(57) ABSTRACT

The present disclosure discloses an artificial femoral prosthesis (100) for knee arthroplasty, a tibial prosthesis (150), a medial femoral unicompartmental prosthesis (201), a lateral femoral unicompartmental prosthesis (301), and a femoral trochlear prosthesis (401). The femoral prosthesis (100) comprises: a medial condyle portion (51) and a medial trochlear portion (131), wherein an articular surface of the medial condyle portion appears in a sagittal section as an arc of a first ellipse (38), and an articular surface of the medial trochlear portion appears in the sagittal section as an arc of a second ellipse or circle (40); and lateral members (91, 141), comprising a lateral trochlear portion (141) and a lateral condyle portion (91), wherein an articular surface of the lateral trochlear portion appears in the sagittal section as an arc of a third ellipse or circle (80), and an articular surface of the lateral condyle portion appears in the sagittal section as an arc of a fourth ellipse (78). The prostheses according to the above embodiments of the present disclosure can better conform to geometric shapes of normal femoral (Continued)

condyles of humans, thereby simplifying greatly design of parameter values for different models of femoral prostheses.

16 Claims, 11 Drawing Sheets

(52) U.S. Cl.
CPC .... *A61F 2/389* (2013.01); *A61F 2002/30125* (2013.01); *A61F 2002/30131* (2013.01); *A61F 2002/30327* (2013.01); *A61F 2002/3863* (2013.01)

(56) References Cited

U.S. PATENT DOCUMENTS

| | | | |
|---|---|---|---|
| 2012/0310362 A1* | 12/2012 | Li | A61F 2/38 623/20.32 |
| 2015/0088264 A1 | 3/2015 | Li et al. | |
| 2015/0342739 A1 | 12/2015 | Mahfouz | |

FOREIGN PATENT DOCUMENTS

| CN | 104068948 A | 10/2014 |
|---|---|---|
| CN | 204709084 U | 10/2015 |
| CN | 205849593 U | 1/2017 |
| CN | 206120506 U | 4/2017 |
| EP | 0681817 A1 | 11/1995 |
| FR | 2663839 A1 | 1/1992 |
| JP | 08506042 | 7/1996 |
| JP | 2011518645 A | 6/2011 |
| WO | WO-2015076326 A1 | 5/2015 |

OTHER PUBLICATIONS

"Japanese Appliccation Serial No. 2019-502130, Notification of Refusal dated May 20, 2020", w/ English Translation, (Jun. 5, 2020), 6 pgs.

"Japanese Appliccation Serial No. 2019-502130, Notification of Refusal dated Sep. 18, 2019", w/ English Translation, (Sep. 18, 2019), 10 pgs.

"European Application Serial No. 17773202.1, European Search Report dated Feb. 4, 2020", (Feb. 4, 2020), 14 pgs.

"International Application Serial No. PCT/CN2017/078397 Written Opinion dated Jun. 28, 2017", (Jun. 28, 2017), 16 pgs.

"International Application Serial No. PCT/CN2017/078397, International Search Report dated Jun. 28, 2017", w/ English Translation, (Jun. 28, 2017), 8 pgs.

"International Application Serial No. PCT/CN2017/078397, Written Opinion dated Jun. 28, 2017", (Jun. 28, 2017), 6 pgs.

\* cited by examiner

ARTIFICIAL PROSTHESIS FOR KNEE ARTHROPLASTY

PRIORITY APPLICATIONS

This application is a U.S. National Stage Filing under 35 U.S.C. 371 from International Application No. PCT/CN2017/078397, filed on Mar. 28, 2017, and published as WO2017/167172 on Oct. 5, 2017, which claims the benefit of priority to Chinese Application No. 201610202287.5, filed on Mar. 31, 2016 and Chinese Application No. 201610196679.5, filed on Mar. 31, 2016; the benefit of priority of each of which is hereby claimed herein, and which applications and publication are hereby incorporated herein by reference in their entirety.

TECHNICAL FIELD

The present disclosure relates to the artificial knee arthroplasty technique, and more particularly, to artificial femoral and tibial prostheses for knee arthroplasty, and a prosthesis for unicompartmental arthroplasty applied to early-stage osteoarthritis in a medial compartment and a lateral compartment of a knee joint, and a trochlea joint.

BACKGROUND

Artificial Total Knee Arthroplasty (TKA) is the best way to treat advanced osteoarthritis, rheumatoid arthritis or traumatic arthritis. According to the reports from the Agency for Healthcare Research and Quality, there are more than 600,000 TKA surgeries in the United States, with a total cost up to tens of billions of dollars per year. Typically, a distal part of a femur undergoing a TKA surgery is partially resected to receive elements of a femoral prosthesis, and a proximal part of a tibia is partially resected to receive elements of a tibial prosthesis. Geometric features of an articular surface of the components of the femoral prosthesis directly affect functions of the knee joint after the surgery, and therefore it is very important to design a femoral prosthesis. The more a femoral components replicate a normal morphology of a distal femur, the more a patient undergoing a surgery will obtain a normal kinematics and sensation.

It is generally believed that the femoral condyles are represented by circles that rotate around a fixed axis. According to this theory, a TKA femoral prosthesis design using a single radius of curvature was proposed, as shown in FIG. 1. The principle for designing this femoral prosthesis 1 is to consider a medial femoral condyle and a lateral femoral condyle as arcs of circles having similar radii. Centers of the two circles do not coincide, and a line for connecting the centers is considered to coincide with the TransEpicondylar Axis (TEA), i.e., a line for connecting the vertexes of the medial femoral condyle and the lateral femoral condyle. That is, the distance from TEA to the cartilage surface of the distal femoral condyle is almost equal to the distance from TEA to the posterior femoral condyle. This kind of single-radius femoral prosthesis is considered by more and more scholars to be one of the important causes of flexion limitation after a surgery due to the lack of an posterior offset value of the femoral condyle. Knee joint postoperative kinematics are also significantly different from that of a normal knee. At the same time, a symmetry design of posterior condyles of a medial and a lateral side does not follow the tension characteristics of collateral ligaments when the knee flexion, and which is considered to be a reason of flexion instability.

The femoral condyles was also considered by some scholars as ahelical shape with a un-fixed rotational axis, i.e. an instantaneous centers. FIG. 2 illustrates a progressive radius femoral component according to the related art, wherein the condyle of the TKA femoral prosthesis uses the design principle of an instantaneous center. For the femoral prosthesis 21 designed using this principle, a contour of an articular surface of the femoral condyle is considered to be a helical shape and the femoral condyle is considered to be composed of a plurality of curved surfaces with different circular radii. However, the method of designing a prosthesis using this principle is extremely cumbersome.

In the 1990s, scholars put their views again on the femoral condyles was circular with a fixed rotational axis. In particular, the application of nuclear magnetic resonance sagittal scanning makes these researchers firmly believe that the femoral condyle is composed of multiple circles in a sagittal section. For example, a contour of the distal femur is considered to be composed of three or four circles having different radii, and centers of these circles are separated from each other, as shown in FIG. 3. For a TKA femoral prosthesis 31 designed according to this principle, in a flexion and extension process of a knee joint, a rotational center of a femoral condyle may suddenly jump from one center to the next. This sudden large jump of the rotational center may impair the stability of the knee joint prosthesis and cause wear of the polyethylene.

A knee joint is divided into three compartments, which are a medial compartment, a lateral compartment and a patellofemoral compartment respectively. Early-stage knee joint osteoarthritis (OA) may involve any compartment, but especially involves the medial compartment of the knee joint. At this condition, the disphyseal axis of the lower extremity located on the medial side (varus deformity), which results in excessive wear on the medial compartment, which cause the cartilage of the medial femoral condyle and the corresponding medial tibial plateau to become thin and exfoliated. Typical symptoms of the OA in the medial compartment are varus deformity, pain and joint lock, osteophyte formation, and relaxation of the lateralcollateral ligament. A conservative or non-surgical treatment (such as non-steroidal anti-inflammatory analgesics, nutrition protection drugs for an articular cartilage, intra-articular injection of hyaluronic acid, knee joint brace, etc.) has only a limited therapeutic effect on patients with mild OA. When the conservative treatment is ineffective, an unicompartmental knee arthroplasty (UKA) for the medial compartment is an effective treatment manner. The UKA for the medial compartment is to resect the articular surface of the tibiofemoral joint, that is, the articular cartilage surface which directly contacts with the medial tibial plateau during flexion and extension, and the corresponding articular cartilage surface of the tibial plateau. The purpose of UKA is to preserve a normal articular structure as much as possible with minimal surgical trauma, so as to ultimately achieve functional recovery, while preserving sufficient residual bone mass for the possibility of total knee arthroplasty revision. Moreover, with the improvement of materials and processing technology, the more suitable choice of indications, the improvement of surgical techniques, the efficacy of the UKA for the medial compartment has been increasingly accepted. The incidence of OA in the lateral compartment and the patellofemoral compartment is significantly less than that of OA in the medial compartment, but the treatment principle for OA in the lateral compartment and the patellofemoral compartment is the same as that for OA in the medial compartment, and if necessary, UKA will be performed.

UKA prostheses for the medial compartment and the lateral compartment may be further divided into tibial UKA prostheses (UKA prostheses of medial and lateral tibial plateaus) and femoral UKA prostheses (UKA prostheses of a medial femoral condyle and a lateral femoral condyle); and UKA prostheses for the patellofemoral compartment are divided into a trochlear (portion) UKA prosthesis and a patellar prosthesis. The design of the femoral UKA prosthesis is more important than the tibial UKA prosthesis because it directly affects functions of the knee joint after a surgery. At present, it is consensus that a femoral UKA prosthesis which replicates the normal geometric features of medial and lateral femoral condyles can provide kinematics closest to a normal knee joint. However, the geometric features of the medial femoral condyle and the lateral femoral condyle are extremely complex and no consensus has been reached. It was widely accepted that the medial femoral condyle and the lateral femoral condyle were circular and are rotated around a fixed axis. Later, some scholars proposed that the medial femoral condyle and the lateral femoral condyle were helical, and the rotational axis was not fixed, but there were instantaneous rotational centers. In the 1990s, scholars renewed the view that the medial femoral condyle and the lateral femoral condyle were circular and rotational axis thereof was fixed. In particular, the application of nuclear magnetic resonance scanning makes these researchers firmly believe that the medial femoral condyle and the lateral femoral condyle are composed of two circles in a sagittal section. These different theories led to different biomechanical and kinematic experimental results and directly affect the design of the UKA prosthesis of the medial femoral condyle and the lateral femoral condyle. For example, according to the theory that the femoral condyle is circles having a single radius curvature, the Oxford unicompartmental prosthesis was designed; according to the theory that the femoral condyle is composed of two or more circles, the Miler-Galante prosthesis was designed, etc. However, the current UKA prostheses of the medial femoral condyle and the lateral femoral condyle have more or less disadvantages. For example, although the Oxford Unicompartmental prosthesis (Oxford UKA) has good long-term follow-up results, a shape of the prosthesis does not match a real shape of the femoral condyle, which results in a deep gap exists between the prosthesis and the femoral trochlea; and as a design feature of circles having a single radius curvature, the Oxford unicompartmental prosthesis cannot restore the mechanical alignment of lower extremity of a patient having varus deformity. Shapes of other types of UKA prostheses (two or more circles) often do not well match the medial femoral condyle and the lateral femoral condyle during a surgery. This leads to the patella impinge on the overhang of prosthesis during knee flexion, which can cause pain and surgical failure. A geometry of a femoral trochlea is a basis for designing a femoral trochlear prosthesis, but geometrical features of the femoral trochlea are more complicated and difficult to replicate, and therefore the UKA prosthesis of the trochlea is simply designed to have aV shape groove and replace the surface of the patella accordingly.

The related technology of UKA prostheses i.e. the medial femoral condyle and the lateral femoral condyle and the UKA prosthesis of the femoral trochlea do not well match the real articular shape of the medial and lateral femoral condyle and trochlea. This shape mismatching causes the impingement of the patella on the prosthesis in the flexion process of the knee joint, which leads to pain and aseptic loosening, and failure finally. Even if the Oxford unicompartmental prosthesis has a slightly less chance of impingement, it is designed using a principle that the medial femoral condyle appears as circle having a single radius curvature. This results in that there is a deep gap between the anterior of the UKA prosthesis and the residual bone in the medial femoral condyle. Although there is no clinical evidence that this gap has an effect on knee joint kinematics or prosthesis lifetime, in fact the most distal end of the femur is located in this gap, and its height cannot be restored, thereby causing failure in correction of the varus deformity of the knee joint. If the prosthesis must be placed at a higher position in order to correct the varus deformity, this may lead to the impact of the patella on the prosthesis in the flexion process, and the Oxford unicompartmental surgery technique does not loosen the collateral ligament, which aims to prevent the dislocation of a mobile tray.

SUMMARY

In view of one or more problems in the related art, there is proposed a femoral prosthesis for artificial knee arthroplasty according to the present disclosure.

According to an aspect of the present disclosure, there is disclosed a femoral prosthesis for artificial knee arthroplasty, comprising:

medial members, comprising a medial condyle portion and a medial trochlear portion, wherein an articular surface of the medial condyle portion appears in a sagittal section as an arc of a first ellipse (38, the ellipse of the medial femoral condyle), and an articular surface of the medial trochlear portion appears in the sagittal section as an arc of a second ellipse or circle (40, the ellipse or circle of the medial femoral trochlea); and lateral members, comprising a lateral trochlear portion and a lateral condyle portion, wherein an articular surface of the lateral trochlear portion appears in the sagittal section as an arc of a third ellipse or circle (80, the ellipse or circle of the lateral femoral trochlea), and an articular surface of the lateral condyle portion appears in the sagittal section as an arc of a fourth ellipse (78, the ellipse of the lateral femoral condyle).

According to some embodiments, an articular surface of a most concave portion of a trochlear groove between the medial trochlear portion and the lateral trochlear portion is an arc of a fifth circle (70, the most concave portion of the trochlear groove) in the sagittal section.

According to some embodiments, a major axis of the first ellipse is perpendicular to a disphyseal axis of a femur, and a center of the first ellipse corresponds to an attachment point of a medial collateral ligament of the medial femoral condyle.

According to some embodiments, a major axis of the fourth ellipse is angled clockwise relative to a major axis of the first ellipse, and a center of the fourth ellipse corresponds to the an attachment point of a lateral collateral ligament of the lateral femoral condyle.

According to some embodiments, a center of the first ellipse and a center of the fourth ellipse coincide in the sagittal section, and a line for connecting the centers is in a direction of the TransEpicondylar Axis (TEA), and is perpendicular to the Whiteside line.

According to some embodiments, a major axis of the second ellipse is perpendicular to a major axis of the first ellipse, a center of the second ellipse or circle and a center of the third ellipse or circle coincide in the sagittal section, and a line for connecting the centers is in a direction of the TransEpicondylar Axis (TEA), and is perpendicular to the Whiteside line.

According to some embodiments, a major axis and a minor axis of the first ellipse intersect with a major axis and a minor axis of the second ellipse to form a rectangle having a length between 8 mm and 16 mm and a width between 4 mm and 12 mm.

According to some embodiments, an angle between a line for connecting a center of the first ellipse and a center of the second ellipse and a major axis of the first ellipse ranges from 25 degrees to 35 degrees.

According to some embodiments, centers of all corresponding first ellipses on various sagittal planes coincide in the sagittal section, and major axes and minor axes of the first ellipses are in the same direction respectively. All the first ellipses form a complete shape of medial femoral condyle portion in a three-dimensional space, and a line for connecting all the centers coincides with the TransEpicondylar Axis (TEA), and is perpendicular to the Whiteside line.

According to some embodiments, centers of all fourth ellipses on various sagittal planes coincide in the sagittal section, and major axes and minor axes of the fourth ellipses are in the same direction respectively. All the fourth ellipses form a shape of a complete shape of lateral femoral condyle portion in a three-dimensional space, and a line for connecting all the centers coincides with the TransEpicondylar Axis (TEA), is perpendicular to the Whiteside line, and coincides with a line for connecting centers of the medial femoral condyle.

According to some embodiments, centers of all second ellipses or circles on various sagittal planes coincide in the sagittal section, and the second ellipses or circles form a complete shape of articular surfaces of a medial femoral trochlea in a three-dimensional space.

According to some embodiments, when the articular surfaces of the medial femoral trochlea are concentric ellipses, major axes and minor axes of these ellipses are in the same direction respectively, the ellipses have different eccentricities, sizes of these ellipses are ranked in a Fibonacci sequence, and a line for connecting all the centers is parallel to the TransEpicondylar Axis (TEA) and is perpendicular to the Whiteside line.

According to some embodiments, centers of all third ellipses or circles on various sagittal planes coincide in the sagittal section, and the third ellipses or circles form a complete shape of articular surfaces of a lateral femoral trochlea in a three-dimensional space.

According to some embodiments, when the articular surfaces of the lateral femoral trochlea are concentric circles, a line for connecting all the centers is parallel to the TransEpicondylar Axis (TEA), is perpendicular to the Whiteside line, and coincides with a line for connecting centers of the articular surfaces of the medial femoral trochlea.

According to some embodiments, a posterior portion of the lateral condyle portion is shorter than and lower than a posterior portion of the medial condyle portion in the sagittal section.

According to some embodiments, an anterior edge of the lateral trochlear portion is longer than and higher than an anterior edge of the medial trochlear portion in the sagittal section.

According to some embodiments, geometric design parameters of inside and outside structures of the entire femoral prosthesis are determined by the relationship and size parameters between the first ellipse and the second ellipse.

According to some embodiments, an articular surface of the medial condyle portion in a coronal section is represented as an arc of the sixth circle (94, the coronal circle of the medial femoral condyle), which has a center coincident with a center of the first ellipse and a radius equal to a semi-minor axis of the first ellipse.

According to some embodiments, the arc of the sixth circle representing the articular surface of the medial condyle portion in the coronal section has an angle ranging from 50 degrees to 90 degrees.

According to some embodiments, an articular surface of the lateral condyle portion in a coronal section is represented as an arc of the seventh ellipse (96, the coronal ellipse of lateral femoral condyle), which has a center coincident with a center of the fourth ellipse, and an internal rotational angle of a major axis of the ellipse relative to a TransEpicondylar Axis (TEA) in the coronal section ranges from 25 degrees to 35 degrees.

According to some embodiments, the arc of the seventh eclipse representing the articular surface of the lateral condyle portion in the coronal section has an angle ranging from 50 degrees to 90 degrees.

According to some embodiments, the articular surface of the lateral condyle portion in the coronal section is represented as an arc of a circle, which has a center coincident with a center of the fourth ellipse, and a radius equal to a semi-minor axis of the fourth ellipse.

According to some embodiments, an inter-condylar structure of the prosthesis is adjusted to adapt to a cruciate ligament retaining-type prosthesis or a posterior stabilizing-type prosthesis or other revision-type prostheses or an individualized 3D printed prosthesis, or a non-patella arthroplasty-type prosthesis, a patella arthroplasty-type prosthesis, or a kinematic alignment-type prosthesis or an assembly-type prosthesis.

According to some embodiments, a width of the prosthesis on coronal section is directly related to size parameters of the circle of the medial femoral condyle and the ellipse of the lateral femoral condyle in the coronal section.

According to some embodiments, an arc of the first ellipse has an angle ranging from 150 degrees to 200 degrees on sagittal section, and an arc of the fourth ellipse has an angle ranging from 120 degrees to 160 degrees on sagittal section.

According to another aspect of the present disclosure, there is provided a tibial prosthesis for use with the femoral prosthesis for artificial knee arthroplasty described above, wherein a shape of the tibial prosthesis in a coronal section comprises a medial tibial plateau surface and a lateral tibial plateau surface, wherein the medial tibial plateau surface has a circular concave shape adapted to the circle of the medial femoral condyle in the coronal section, and the lateral tibial plateau surface has an elliptical concave shape adapted to the ellipse of the lateral femoral condyle in the coronal section.

According to some embodiments, a bottom surface of the tibial prosthesis is designed with an inner rotational angle of 0 degree, 1 degrees, 2 degrees and 3 degrees to adapt to an osteotomy surface of a kinematic alignment-type tibial plateau.

According to yet another aspect of the present disclosure, there is provided a femoral prosthesis for artificial knee arthroplasty, comprising:

medial members, comprising a medial condyle portion and a medial trochlear portion, wherein an articular surface of the medial condyle portion appears in a sagittal section as an arc of a first circle, and an articular surface of the medial trochlear portion appears in the sagittal section as an arc of a second ellipse or circle; and lateral members, comprising a lateral trochlear portion and a lateral condyle portion, wherein an articular surface of the lateral trochlear portion appears in the sagittal section as an arc of a third ellipse or circle, and an articular surface of the lateral condyle portion appears in the sagittal section as an arc of a fourth ellipse.

According to still another aspect of the present disclosure, there is provided a femoral prosthesis for artificial knee arthroplasty, comprising:

medial members, comprising a medial condyle portion and a medial trochlear portion, wherein an articular surface of the medial condyle portion appears in a sagittal section as an arc of a first ellipse, and an articular surface of the medial trochlear portion appears in the sagittal section as an arc of a second ellipse or circle; and lateral members, comprising a lateral trochlear portion and a lateral condyle portion, wherein an articular surface of the lateral trochlear portion appears in the sagittal section as an arc of a third ellipse or circle, and an articular surface of the lateral condyle portion appears in the sagittal section as an arc of a fourth circle.

According to a further aspect of the present disclosure, there is provided a medial femoral unicompartmental prosthesis, comprising:

an articular surface, which is a surface in contact with a medial patella and a medial tibial plateau during motion of a knee joint, wherein the articular surface appears as an arc of a first ellipse in a sagittal section, and appears as an arc of a sixth circle in a coronal section; and an inside structure which is a portion adjacent to an osteotomy surface of a femoral condyle portion and a bone cement after the prosthesis is placed, wherein the inside structure appears as a posterior condyle of the inside structure in a straight section, and a distal portion of the inside structure conformal to the arc of the articular surface.

According to some embodiments, the medial femoral unicompartmental prosthesis further comprises:

a first pillar disposed on the inside side and corresponding to a center of the first ellipse; and a second pillar disposed on the inside side and corresponding to a focus of the first ellipse.

According to some embodiments, a locking screw hole is formed at an anterior end of the medial femoral unicompartmental prosthesis, and is formed so that a direction in which a locking screw is inserted is different from a direction of the first pillar and the second pillar.

According to some embodiments, a major axis of the first ellipse is perpendicular to a disphyseal axis of a femur, and a center of the first ellipse corresponds to an attachment point of a medial collateral ligament of the medial femoral condyle.

According to some embodiments, corresponding first ellipses on various sagittal planes form a shape of a complete medial femoral unicompartmental prosthesis in a three-dimensional space, centers of the first ellipses coincide in the sagittal section, major axes and minor axes of the first ellipses are in the same direction respectively, and a line for connecting all the centers coincides with a TransEpicondylar Axis (TEA), and is perpendicular to a Whiteside line.

According to some embodiments, from the perspective of an axial section, the prosthesis is placed to be parallel to a Whiteside line and perpendicular to a TransEpicondylar Axis (TEA), there is a straight edge on a lateral side of the prosthesis, the straight edge is parallel to the Whiteside line and is perpendicular to the TEA, a medial arc edge is arc-shaped to adapt to a shape of a distal end of the medial femoral condyle, an anterior arc edge has a curvature corresponding to parameters of a circle of an abrasive tool, and a bottom has a curvature of the sixth circle in the coronal section.

According to some embodiments, the arc of the first ellipse has an angle ranging from 150 degrees to 200 degrees, and the arc of the sixth circle has an angle ranging from 50 degrees to 90 degrees.

According to a further aspect of the present disclosure, there is provided a lateral femoral unicompartmental prosthesis, comprising:

an articular surface, which is a surface in contact with a lateral patella and a lateral tibial plateau during motion of a knee joint, wherein the articular surface appears as an arc of a fourth ellipse in a sagittal section, and appears as an arc of a seventh ellipse in a coronal section; and an inside structure which is a portion adjacent to an osteotomy surface of a femoral condyle portion and a bone cement after the prosthesis is placed, wherein the inside structure appears as a posterior condyle in a straight section, and a distal end conformal to the arc of the articular surface.

According to some embodiments, the lateral femoral unicompartmental prosthesis further comprises:

a third pillar disposed on the inside side and corresponding to a focus of the fourth ellipse.

According to some embodiments, a locking screw hole is formed at a distal end of the lateral femoral unicompartmental prosthesis, and is formed so that a direction in which a locking screw is inserted is different from a direction of the third pillar.

According to some embodiments, corresponding the fourth ellipses on various sagittal planes form a shape of a complete lateral femoral unicompartmental prosthesis in a three-dimensional space, centers of the fourth ellipses coincide in the sagittal section, major axes and minor axes of the fourth ellipses are in the same direction respectively, and a line for connecting all the centers coincides with a TransEpicondylar Axis (TEA), and is perpendicular to a Whiteside line.

According to some embodiments, from the perspective of an axial section, the prosthesis is placed to be parallel to a Whiteside line and perpendicular to a TransEpicondylar Axis (TEA), there is a straight edge on a medial side of the prosthesis, the straight edge is parallel to the Whiteside line and is perpendicular to the TEA, a lateral arc edge is arc-shaped to adapt to a shape of a distal end of the lateral femoral condyle, an anterior arc edge has a curvature corresponding to curvature parameters of a circle, and a bottom has a curvature of an arc of the seventh ellipse in the coronal section.

According to some embodiments, the arc of the fourth ellipse has an angle ranging from 120 degrees to 160 degrees, and the arc of the seventh ellipse has an angle ranging from 50 degrees to 90 degrees.

According to a further aspect of the present disclosure, there is provided a femoral trochlear prosthesis, comprising:

an articular surface, which is a surface in contact with an articular surface of a patella during motion of a knee joint, wherein the articular surface appears in a sagittal section as a set of an arc of a second ellipse or circle and an arc of a third ellipse or circle; and an inside structure which is a portion adjacent to an osteotomy surface of a femoral trochlear portion and a bone cement after the prosthesis is placed, wherein the surface appears as an inside structure conformal to an articular surface of the femoral trochlea.

According to some embodiments, the second ellipse or circle and the third ellipse or circle are arranged concentrically, and a concentric axis is spatially parallel to a TEA and is spatially perpendicular to a Whiteside line.

According to some embodiments, the femoral trochlear prosthesis has a pillar at a center thereof and four surrounding locking screw holes in which locking screws are mounted.

The prosthesis according to the above embodiments of the present disclosure has a geometry closer to that of a femoral condyle of a normal human body, which simplifies the design parameter values of various models of femoral prostheses.

BRIEF DESCRIPTION OF THE DRAWINGS

In order to more clearly illustrate the technical solutions in the embodiments of the present disclosure or the prior art, the accompanying drawings used in the description of the embodiments or the prior art will be briefly described below, and it will be apparent to those skilled in the art that other accompanying drawings can be obtained according to these accompanying drawings without any creative work. In the accompanying drawings.

DETAILED DESCRIPTION

Figure 1:
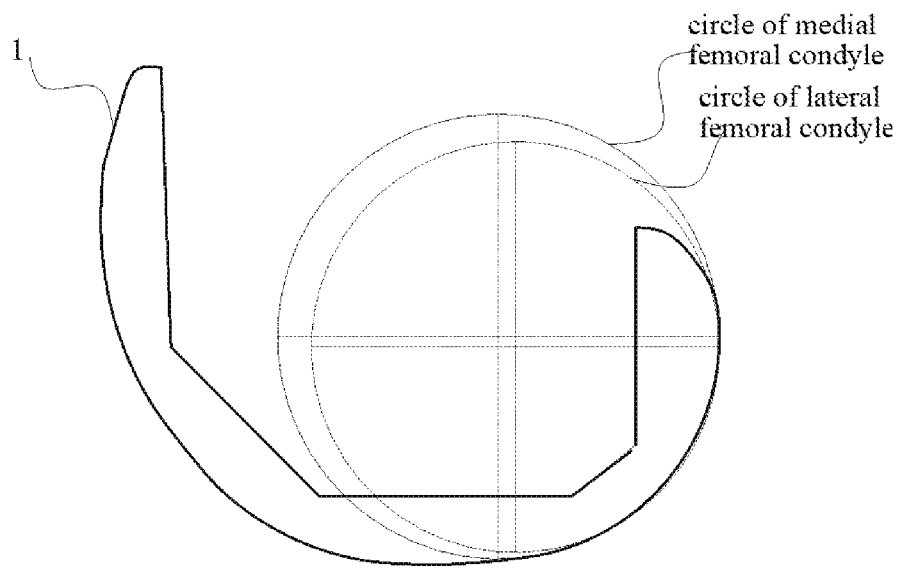
FIG. 1 is a schematic view illustrating a femoral prosthesis in the related art.
Figure 2:
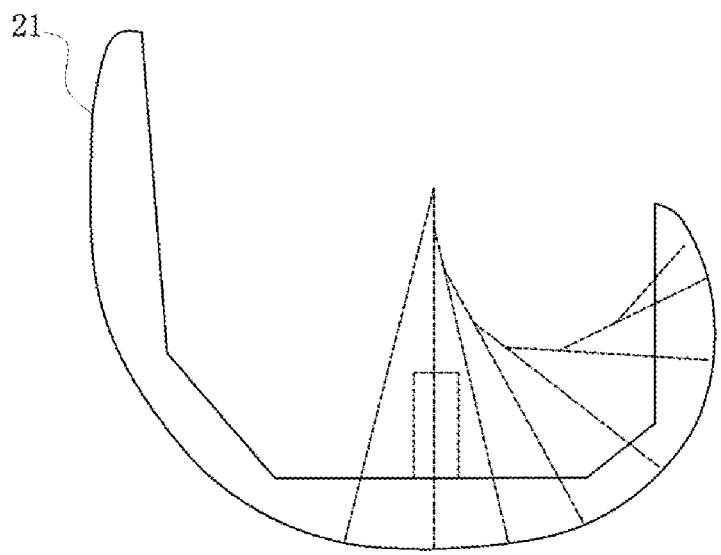
FIG. 2 is a schematic view illustrating another femoral prosthesis in the related art.
Figure 3:
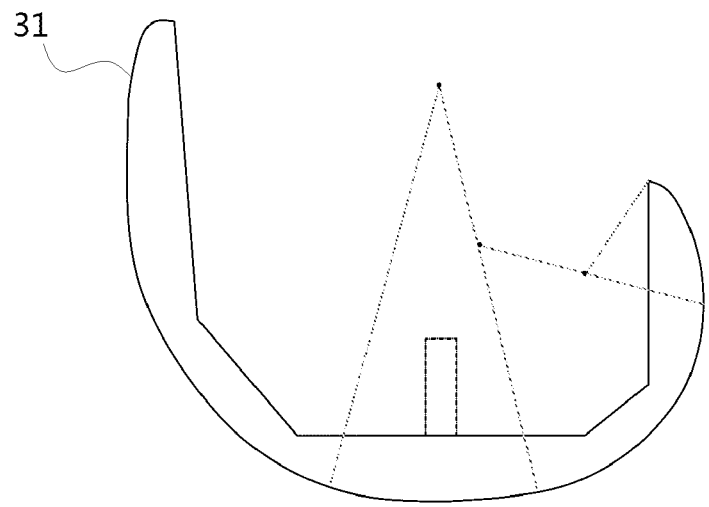
FIG. 3 is a schematic view illustrating yet another femoral prosthesis in the related art.

Specific embodiments of the present disclosure will be described in detail below. It is to be understood that the embodiments described here are for illustrative purposes only and are not intended to limit the present disclosure. In the following description, numerous specific details are set forth in order to provide a thorough understanding of the present disclosure. However, it will be apparent to those of ordinary skill in the art that the present disclosure may be practiced without these specific details. In other instances, well-known materials or methods have not been specifically described in order to avoid obscuring the present disclosure.

A shape of the TKA femoral prosthesis according to the embodiments of the present disclosure has geometric features closer to those of a femoral condyle portion and a femoral trochlear portion of a normal human body. An elliptical principle and a design method applied to the femoral prosthesis will be described in detail in one or more embodiments below. One or more embodiments will be presented in illustrations. However, these illustrations and descriptions do not limit inventive content to be protected by that the present disclosure. Each illustration and description will be associated with other illustrations.

According to one or more embodiments, elements of the femoral prosthesis according to the present disclosure comprise an articular surface of the femoral prosthesis and an inside structure of the femoral prosthesis. Here, the articular surface of the femoral prosthesis is further divided into a medial condyle, a lateral condyle, a medial trochlea, a lateral trochlea, and a most concave plane of the trochlea of the femoral prosthesis. The inside structure of the femoral prosthesis is further divided into an anterior section, a distal section, a posterior section, an anterior slope section, and a posterior slope section of the femoral prosthesis. Specifically, the medial condyle of the femoral prosthesis refers to a portion which is jointly connected to a medial compartment of a tibia during the motion of a knee joint; the lateral condyle of the femoral prosthesis refers to a portion which is jointly connected to a lateral compartment of the tibia during the motion of the knee joint; the medial femoral trochlea refers to a portion which corresponds to a medial side of the patella during the motion of the knee joint; the lateral femoral trochlea refers to a portion which corresponds to a lateral surface of the patella during the motion of the knee joint; and the most concave plane of the femoral trochlea refers to a plane where the medial femoral trochlea is intersected with the lateral femoral trochlea, which corresponds clinically to a position of a Whiteside line. The anterior section of the femoral prosthesis refers to a portion which is adjacent to an osteotomy surface of an anterior femoral condyle after the femoral prosthesis is placed; the distal section of the femoral prosthesis refers to a portion which is adjacent to an osteotomy surface of a distal femoral condyle after the femoral prosthesis is placed; the posterior section of the femoral prosthesis refers to a portion which is adjacent to an osteotomy surface of a posterior femoral condyle after the femoral prosthesis is placed; the anterior slope section of the femoral prosthesis refers to a portion which is connected to the anterior section and the distal section; and the posterior slope section of the femoral prosthesis refers to a portion which is connected to the distal section and the posterior section. It should be illustrated that as used herein, "anterior" refers to pointing to a ventral side of a human body; "posterior" refers to pointing to a back side of the human body; "near" refers to pointing to a head side of the human body; "distal" refers to pointing to a tail side of the human body, and so on. Similarly, descriptions of "sagittal section", "coronal section" and "axial section" are defined to be the same as those in terms of anatomical planes. "Horizontal axis" points to "anterior" and "posterior" directions and is parallel to the ground; and "vertical axis" points to "distal" and "proximal" directions and is perpendicular to the ground. In general, the "most distal point" of an element of the femoral prosthesis refers to the most distal contact point established with a corresponding tibial support when the knee joint is fully extended; and the "most posterior point" of the element of the femoral prosthesis is a point having a maximum posterior offset of the femoral prosthesis, which is perpendicular to the "most distal point". The "most anterior point" of the element of the femoral prosthesis is a point having a maximum anterior offset of the femoral prosthesis, which is opposite to the "most posterior point".

The embodiments described in the present disclosure are shown as elements of the femoral prosthesis on the left side. The elements of the femoral prosthesis on the right side are mirrored relative to the elements of the femoral prosthesis on the left side in a sagittal section. Therefore, it is stated that the principle of the features of the femoral prosthesis described here is equally applicable to left knee joint or right knee joint configuration. It is to be understood that the design of the femoral prosthesis according to the present disclosure comprises a "Cross-ligament Retention (CR)" prosthesis. Some other contemplated designs comprise a "Post-Stabilized (PS)" prosthesis and a "Middle Level-Constrained (MLC)" prosthesis etc. Here, the CR prosthesis is relative to the PS prosthesis, and a cam structure on the elements of the femoral prosthesis and a post structure on elements of the tibial prosthesis are omitted. This allows the CR prosthesis to appear between the lateral condyle and the medial condyle as an intercondyal space which is generally open and is not obstructed by the femoral cam structure. The PS prosthesis and the MLC prosthesis may be formed by suitably modifying the femoral prosthesis according to the present disclosure to add the cam structure on the elements of the femoral prosthesis and the post structure on the tibial side. Therefore, all of the principles described in the present disclosure may be used with any potentially contemplated femoral prosthesis design. Although any potentially contemplated femoral prosthesis design may comprise all of the features described here, it is also contemplated that some potentially contemplated femoral prosthesis designs may omit or may be added with some of the features described here, depending on particular applications or requirements in other situations.

According to one or more embodiments of the present disclosure, in the sagittal section, the contour of articular surfaces of the medial condyle and the lateral condyle of the femoral prosthesis are composed of ellipses, and the contour of articular surfaces of the medial trochlea and the lateral trochlea of the femoral prosthesis are composed of ellipses and/or circles; and in the coronal section, the contour of the articular surfaces of the medial condyle and the lateral condyle of the femoral prosthesis are composed of circles and ellipses, respectively.

For example, the medial condyle and the lateral condyle of the femoral prosthesis are designed and constructed according to the principle of ellipse, and each are an arc of an ellipse. The medial femoral condyle is a slightly larger ellipse, which has a major axis parallel to a horizontal line; and the lateral femoral condyle is a slightly smaller ellipse, which has a major axis direction angled clockwise relative to the ellipse of the medial femoral condyle. At the same time, centers of the ellipses of the medial femoral condyle and the lateral femoral condyle coincide in the sagittal section of the femoral prosthesis, and a line for connecting the centers clinically conforms to a direction of TransEpicondylar Axis (TEA).

In another example, in the sagittal section, various sagittal planes of an articular cartilage surface of the medial femoral condyle are a set of ellipses, which form a complete shape of the medial femoral condyle and the lateral femoral condyle in three dimensions. Here, the articular cartilage surface of the medial femoral condyle has a concentric elliptical structure in a direction perpendicular to the TEA line and parallel to the Whiteside line; and the articular cartilage surface of the lateral femoral condyle has a concentric elliptical structure in a direction perpendicular to the TEA line and parallel to the Whiteside line.

According to an embodiment of the present disclosure, the trochlear portion of the femoral prosthesis is designed and constructed according to the principle of a circle and an ellipse. An articular surface of a most concave portion of a femoral trochlear groove is an arc of a circle; an articular surface of the medial femoral trochlea is an arc of an ellipse or circle; and an articular surface of the lateral femoral trochlea is an arc of a circle or ellipse. Here, a major axis direction of the ellipse is perpendicular to a major axis of the ellipse of the medial femoral condyle. Centers of ellipses or circles of the femoral trochlear portion coincide in the sagittal section.

For example, in the sagittal plane, all sections of the femoral trochlea may appear as ellipses or circles. They form a complete femoral trochlear structure in three dimensions. Various sagittal planes of the articular cartilage surface of the medial femoral trochlea is a set of ellipses, major axes and minor axes of these ellipses are in the same direction respectively, and centers of various ellipses are arranged concentrically. However, various ellipses have different eccentricities. Sizes of these ellipses are, for example, ordered in a Fibonacci sequence. All sections of the lateral femoral trochlea appear as circles. Although various circles of the lateral trochlea have different radiuses, projections of centers of the circles are coincident.

A shape of the UKA prosthesis (comprising the medial femoral condyle, the lateral femoral condyle and the articular surface of the femoral trochlea) according to the embodiments of the present disclosure has geometric features closest to those of a femoral condyle portion and a femoral trochlear portion of a normal human body. This elliptical principle and a design method applied to UKA will be described in detail in one or more embodiments below. According to one or more embodiments, elements of the UKA prosthesis according to the present disclosure comprise arthroplasty components for the medial femoral condyle, the lateral femoral condyle, and the femoral trochlea. They may be applied alone in a case of specific unicompartmental osteoarthritis, or may also be applied in combination in a case of dual-compartmental or triple-compartmental osteoarthritis. Specifically, elements of the UKA prosthesis of the medial femoral condyle refers to a portion which is jointly connected to a medial compartment of a tibia during the motion of the knee joint; elements of the UKA prosthesis of the lateral condyle refers to a portion which is jointly connected to a lateral compartment of the tibia during the motion of the knee joint; and elements of the UKA prosthesis of the femoral trochlea refers to a portion which corresponds to a patella during the motion of the knee joint. Here, any of elements of the UKA prosthesis comprises an articular surface of the prosthesis and an inside structure of the prosthesis. It should be illustrated that as used here, "anterior" refers to pointing to a ventral side of a human body; "posterior" refers to pointing to a back side of the human body; "medial" refers to being towards to a central axis of a torso of the human body; "lateral" refers to being away from the central axis of the torso of the human body; "proximal" refers to pointing to a head side of the human body; "distal" refers to pointing to a tail side of the human body, and so on. Similarly, descriptions of "sagittal section", "coronal section" and "axial section" are defined to be the same as those in terms of anatomical planes. "Horizontal axis" points to "anterior" and "posterior" directions and is parallel to the ground; and "vertical axis" points to "distal" and "proximal" directions and is perpendicular to the ground. In general, the "most distal point" of an element of the UKA prosthesis refers to the most distal contact point established with a corresponding tibial side when the knee joint is fully extended; and the "most posterior point" of the element of the UKA prosthesis is a point having a maximum posterior offset from the back of the UKA prosthesis, which is perpendicular to the "most distal point". The "most anterior point" of the element of the UKA prosthesis is a point having a maximum anterior offset from the front of the UKA prosthesis, which is opposite to the "most posterior point".

The embodiments described in the present disclosure are shown as elements of the UKA prosthesis on the left side. The elements of the UKA prosthesis on the right side are mirrored relative to the elements of the UKA prosthesis on the left side in the sagittal section. Therefore, it is stated that the principle of the features of the UKA prosthesis described here is equally applicable to left knee joint or right knee joint configuration. It should be illustrated that the UKA prosthesis design of the femoral trochlea according to the present disclosure comprises a prosthesis in a case of "articular surface with patella arthroplasty" and a prosthesis in a case of "articular surface with non-patella arthroplasty". Here, the UKA prosthesis of the femoral trochlea with "articular surface with patella arthroplasty" is designed with corresponding trochlear groove and angle corresponding to the patella compared with the prosthesis with "articular surface with non-patella arthroplasty".

According to one or more embodiments of the present disclosure, in the sagittal plane, the contour of the articular surfaces of the medial femoral condyle and lateral femoral condyle are composed of ellipses, and the contour of the articular surfaces of the medial trochlea and lateral trochlea are composed of ellipses and/or circles; and in the coronal plane, the contour of the articular surfaces of the medial femoral condyle and lateral femoral condyle are composed of circles and ellipses, respectively.

For example, the UKA prosthesis of the medial femoral condyle is designed and constructed according to the principle of an ellipse in the sagittal section and a circle in the coronal section. In the sagittal section, various planes of an articular surface of the medial femoral condyle are a set of ellipses, which form a complete shape of the medial femoral condyle in three dimensions. Here, the articular cartilage surface of the medial femoral condyle has a concentric elliptical structure in a direction perpendicular to the TEA line and parallel to the Whiteside line; and the articular surface of the medial femoral condyle appears as an arc of a circle in coronal plane.

As another example, the UKA prosthesis of the lateral femoral condyle is designed and constructed according to the principle of an ellipse in the sagittal section and an ellipse in the coronal section. In the sagittal section, various planes of the articular surface of the lateral femoral condyle are a set of ellipses, which form a complete shape of the lateral femoral condyle in three dimensions. The lateral femoral condyle is a slightly smaller than the ellipse of the medial femoral condyle, which has a major axis direction angled clockwise relative to the ellipse of the medial femoral condyle. The articular cartilage surface of the lateral femoral condyle has a concentric elliptical structure in a direction perpendicular to the TEA line and parallel to the Whiteside line. In the coronal section, the articular surface of lateral femoral condyle appears as an arc of an ellipse.

According to an embodiment of the present disclosure, the UKA prosthesis of the femoral trochlea is designed and constructed according to a principle of an ellipse and circle. In the sagittal section, various planes of the femoral trochlea may appear as ellipses or circles. They form a complete femoral trochlear structure in three dimensions. Various sagittal planes of the articular cartilage surface of the medial femoral trochlea are a set of ellipses, major axes and minor axes of these ellipses are in the same direction respectively, and centers of various ellipses are arranged concentrically. However, various ellipses have different eccentricities. Sizes of these ellipses are, for example, ordered in a Fibonacci sequence. All planes of the lateral femoral trochlea appear in a circular shape. Although various circles of the lateral trochlea have different radii, projections of centers of the circles are coincident. A line for connecting the centers of the ellipses and circles of the femoral trochlea is parallel to the TEA line and perpendicular to the Whiteside line. Parameters of the ellipses of the medial femoral condyle and circles on the most concave plane of the femoral trochlea determine a shape of the entire prosthesis and parameters of the major axes and the minor axes.

Figure 4A:
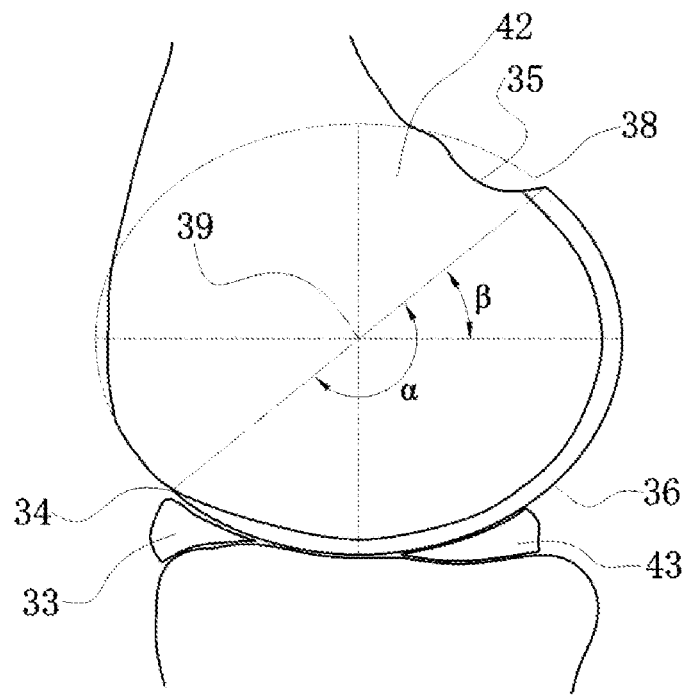
FIG. 4A is a schematic cross-sectional view illustrating a medial condyle of a knee joint of a femoral prosthesis in a sagittal section according to an embodiment of the present disclosure.
Figure 4B:
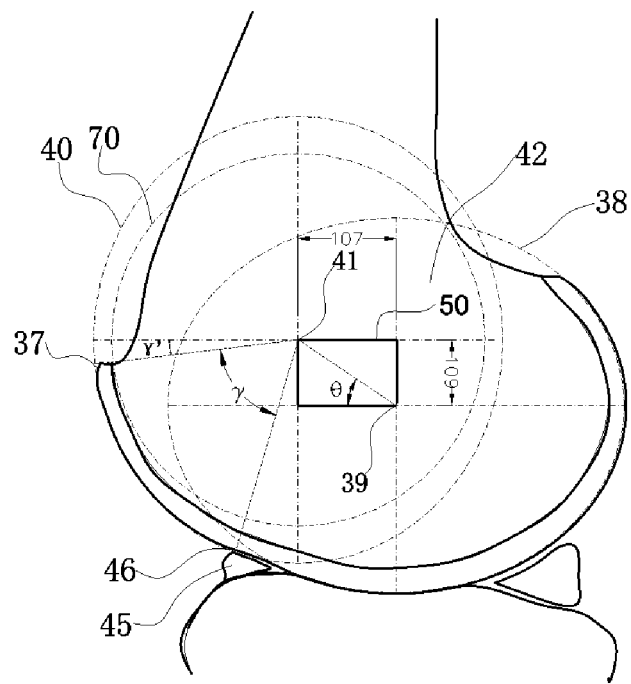
FIG. 4B is a schematic cross-sectional view illustrating a medial trochlea of a knee joint of a femoral prosthesis in a sagittal section according to an embodiment of the present disclosure.
Figure 5:
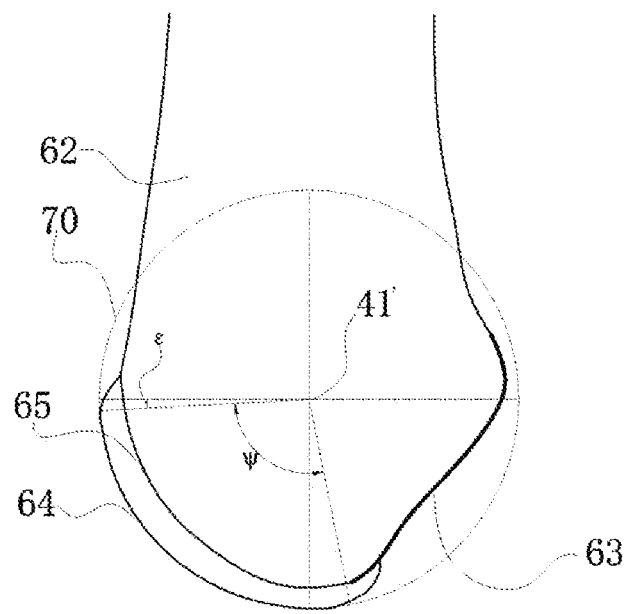
FIG. 5 illustrates a schematic cross-sectional view illustrating a most concave portion of a trochlea in a femoral prosthesis in a sagittal section according to an embodiment of the present disclosure.

For example, the best or most correct manner for scanning the knee joint using the Magnetic Resonance Imaging (MRI) in the sagittal section is that when the knee joint is 0 degree extension position, axial MRI scanning of the knee joint is set to be in a direction of a line for connecting vertexes of the medial femoral condyle and the lateral femoral condyle (TEA orientation), and coronal MRI scanning of the knee joint is set to be in a direction which is tangent to an articular surface of a tibial plateau. Geometric characteristics of the medial femoral condyle may be represented by an ellipse, and belongs to an arc of the ellipse, for example, the arc ranges from 150 degrees to 200 degrees. In one embodiment, a sagittal plane having a maximum posterior offset of the medial femoral condyle is selected, that is, an intermediate plane of the medial femoral condyle. The medial femoral condyle is best-fitted by an ellipse is shown in FIG. 4A. For a segment from an anterior recess 34 that formed by an anterior horn 33 of a medial meniscus on an articular cartilage surface 36 of a medial femoral condyle 42 in extension to a posterior recess 35 that formed by a posterior horn 43 of the medial meniscus on the medial femoral condyle 42 in high flexion, the articular cartilage surface 36 of the medial femoral condyle 42 in this segment is best-fitted by an ellipse 38. The major axis of the ellipse 38 is perpendicular to the mechanical axis of the diaphyseal shaft, and an elliptical center 39 corresponding to an attachment point 123 of a medial collateral ligament of the medial femoral condyle on the axial MRI and coronal MRI. In one embodiment, the ellipse 38 has a semi-major axis of 31 mm, a semi-minor axis of 25 mm, and an eccentricity of 0.591. In another embodiment, the ellipse here has a semi-major axis of 27 mm, a semi-minor axis of 22 mm, and an eccentricity of 0.58. In multiple embodiments, the semi-major axis is between 20 mm and 35 mm, the semi-minor axis is between 16 mm and 30 mm, and the eccentricity is between 0.5 and 0.7. At the same time, an arc length of the articular cartilage surface 36 in the segment may be described through an angle α between lines for connecting a center 39 of the ellipse and the anterior and posterior notches 34 and 35, and an angle β between a line for connecting the center 39 of the ellipse and the posterior notch 35 and the major axis of the ellipse 38. In one embodiment, the angle α is 180 degrees and the angle β is 35 degrees. In another embodiment, the angle α is 190 degrees and the angle β is 40 degrees. In multiple embodiments, the angle α is between 170 and 195 degrees and the angle β is between 20 and 45 degrees. In most cases, there is no articular surface of the medial femoral trochlea in front of the intermediate plane of the medial femoral condyle, that is, the ellipse 38 in the intermediate plane of the medial femoral condyle does not correspond to a plane having a maximum anterior offset of the medial femoral trochlea, and ellipses in the two planes are not in a same scanning section. Therefore, the ellipse 38 of the medial femoral condyle may be projected in the MRI sagittal scanning direction to the plane having a maximum anterior offset of the medial femoral trochlea, as shown in FIG. 4B. For a segment from an anterior recess 46 that formed by an anterior horn 45 of a medial meniscus on the articular cartilage surface 36 of the medial femoral condyle 42 in extension position up to an articular cartilage surface 37 of a medial femoral trochlea in this plane, the articular cartilage surface 37 in this segment may be represented by an arc of an ellipse 40. Although articular surfaces in this segment for femoral trochlea prostheses of some subjects shows as circles, the femoral trochlea prostheses of most subjects show as ellipses. A major axis of the ellipse 40 of the medial femoral trochlea is perpendicular to a major axis of the ellipse 38 in the intermediate plane of the medial femoral condyle. This ellipse 40 is based on the circle 70 on the most concave plane of the femoral trochlea as shown in FIG. 5, and therefore projections of a center 41 of the ellipse 40 and a center 41' of the circle 70 in the most concave plane of the femoral trochlea (FIG. 5) coincide in the sagittal scanning. In one embodiment, the ellipse 40 has a semi-major axis of 29 mm, a semi-minor axis of 27 mm, and an eccentricity of 0.365. In multiple embodiments, the ellipse 40 has a semi-major axis between 20 mm and 35 mm and a semi-minor axis between 20 mm and 30 mm. In general, a difference between the semi-major axis and the semi-minor axis of the ellipse 40 is not large, such as 1 mm, 2 mm, or 3 mm. At the same time, an arc 37 of the articular cartilage surface of the trochlea in this segment may be described through an angle γ between lines for connecting the center 41 and the anterior notch 46 and an end point of the cartilage surface of the trochlea, and an angle γ' between a line for connecting the center 41 and the end point of the cartilage surface of the trochlea and the semi-minor axis of the ellipse 40. In multiple embodiments, the angle γ is between 40 and 80 degrees and the angle γ' is between −5 and 40 degrees.

According to some embodiments, a positional relationship between the center 39 of the ellipse 38 of the medial femoral condyle and the center 41 of the ellipse 40 of the medial femoral trochlea determines a spatial positional relationship between the femoral condyle and the femoral trochlea, which determines the values of the outside parameters and the inside parameters of the femoral prosthesis. The relationship between the femoral trochlea and the femoral condyle may be represented by a rectangle 50 formed by the major axes and the minor axes of the ellipse 38 of the medial femoral condyle and the ellipse 40 of the medial femoral trochlea. In one embodiment, the rectangle 50 has a length 107 of 13 mm and a width 109 of 9 mm. In another embodiment, the rectangle 50 has a length 107 of 12 mm and a width 109 of 7 mm. In multiple embodiments, the length 107 of the rectangle 50 is between 8 mm and 16 mm and the width 109 of the rectangle 50 is between 4 mm and 12 mm. The angle between a line for connecting the centers 39 and 41 of the two ellipse 38 and 40 and the major axis of the ellipse 38 of the medial femoral condyle is 9. In one embodiment, θ is 32 degrees. In another embodiment, θ is 35 degrees. In multiple embodiments, the angle θ ranges between 25 degrees and 35 degrees.

The most concave plane 62 of the femoral trochlea is a plane where the Whiteside line is clinically located, as shown in FIG. 5. This plane 62 is an important basis for determining a geometrical shape of the articular surface of the medial and lateral femoral trochleas. There is only one circle 70 which can best coincide with the articular cartilage surface 64 of the trochlear plane 62, and can best coincide with a circle of a subchondral bone surface 65 of this plane 62 after being scaled down. A projection of the center 41' of the circle 70 in the MRI sagittal scanning coincides with the center 41" of the ellipse 40 of the medial femoral trochlea and the center of the circle 80 of the lateral femoral trachea. The Blumensaat line 63 is clinically encompassed by this circle 70. Similarly to the previous description, the articular cartilage surface 64 of this plane 62 is an arc of the circle 70 and may be represented by a radius of the circle 70 and an angle. An angle between lines for connecting the center 41' and the anterior and posterior boundaries of the articular cartilage surface 64 of the trochlea is ψ; and an angle between the line for connecting the center 41' and the anterior boundary of the articular cartilage surface 64 and the horizontal axis is ε. In one embodiment, the circle 70 has a radius of 24 mm, ψ of 100 degrees, and ε of 0 degrees. In another embodiment, the circle 70 has a radius of 25 mm, ψ of 105 degrees, and ε of 5 degrees. In multiple embodiments, the circle 70 has a radius of 16 mm to 30 mm, ψ ranging from 90 degrees to 125 degrees, and c ranging from −20 degrees to 10 degrees. Further, there is a specific ratio of the radius of the circle 70 relative to a length of the semi-major axis of the ellipse 38 of the medial femoral condyle, for example, 2/5, 3/5 or 3/4.

Figure 6:
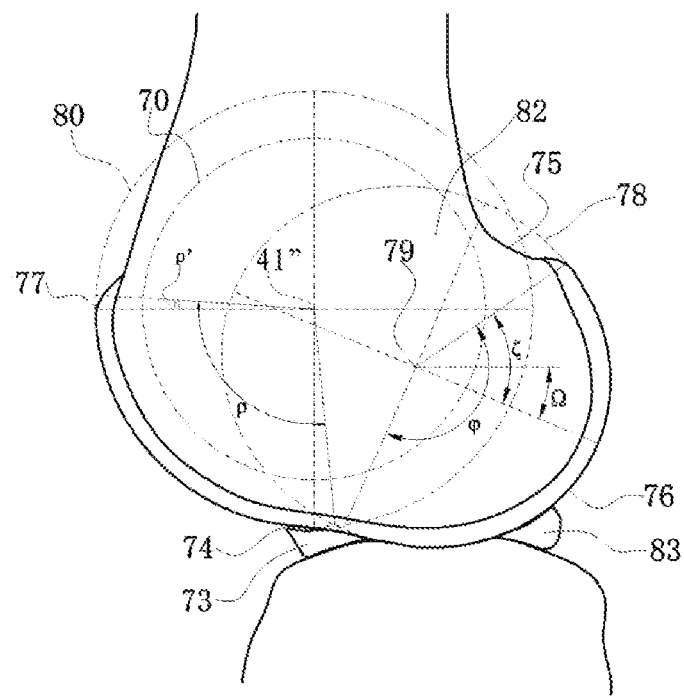
FIG. 6 illustrates a schematic cross-sectional view illustrating a lateral femoral condyle and a femoral trochlea of a knee joint of a femoral prosthesis in a sagittal section according to an embodiment of the present disclosure.
Figure 9A:
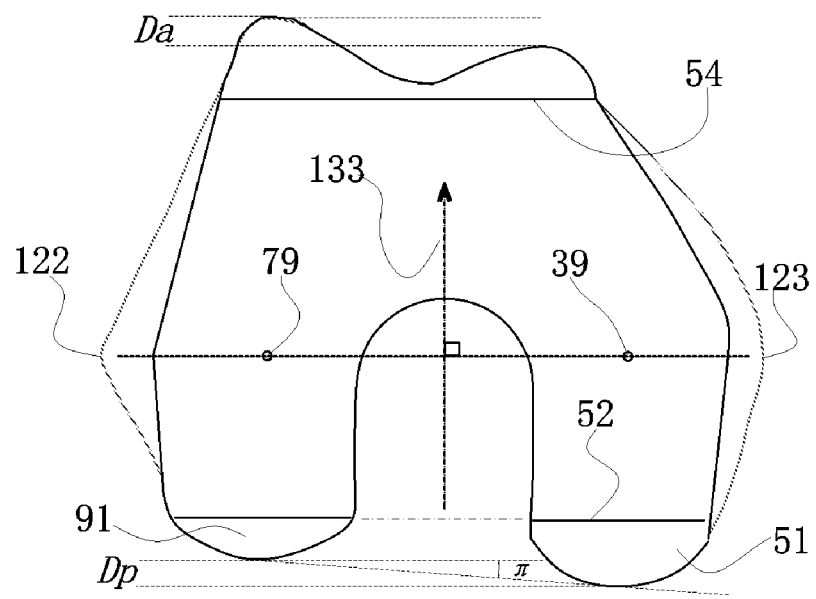
FIG. 9A illustrates a schematic cross-sectional view of a femoral prosthesis in an axial section according to the present disclosure, illustrating asymmetry of an articular surface of the femoral prosthesis and symmetry of an inside structure of the femoral prosthesis, and an intorsion trend of a medial femoral condyle.

According to an embodiment of the present disclosure, a geometry of the lateral femoral condyle may be represented by an ellipse, and belongs to an arc of the ellipse, for example, the arc ranges from 120 degrees to 160 degrees. In one embodiment, a sagittal plane having a maximum posterior offset of the lateral femoral condyle, that is, an intermediate plane of the lateral femoral condyle, is selected. This sagittal plane is also a plane having a maximum anterior offset of the lateral femoral trochlea, and relationships thereof are shown in FIG. 6. For a segment from an anterior recess 74 that is formed by an anterior horn 73 of a lateral meniscus on an articular cartilage surface 76 of a lateral femoral condyle 82 in extension position to a posterior recess 75 that is formed by a posterior horn 83 of the lateral meniscus on an articular cartilage surface of the lateral femoral condyle 82 in a high flexion position, the articular cartilage surface 76 of the lateral femoral condyle 82 in this segment is best-fitted by an ellipse 78. The major axis of the ellipse 78 is rotated clockwise by a certain angle Ω relative to the major axis of the ellipse 38 of the medial femoral condyle, such as 12 degrees in one embodiment, and 18 degrees in another embodiment, and in multiple embodiments, an average value of Ω is between 5 degrees and 25 degrees. A projection of the center 79 thereof in the sagittal section coincides with the center 39 of the ellipse 38 of the medial femoral condyle; and corresponds to an attachment point 122 of the collateral ligament of the lateral femoral condyle in the MRI axial section (FIG. 9A). In one embodiment, the ellipse 78 has a semi-major axis of 30 mm and a semi-minor axis of 26 mm; and in another embodiment, the ellipse 78 has a semi-major axis of 26 mm and a semi-minor axis of 23 mm. In multiple embodiments, the ellipse 78 has a semi-major axis between 21 mm and 33 mm, a semi-minor axis between 16 mm and 30 mm, and an eccentricity between 0.5 and 0.7. At the same time, an arc of the articular surface 76 in this segment may be accurately described by measuring the angle φ between lines for connecting the center 79 and the anterior and posterior recesses 74 and 75, and the angle ζ between the line for connecting the center 79 and the posterior recess 75 and the major axis of the ellipse 81 of the lateral condyle. In one embodiment, φ is 130 degrees and ζ is 40 degrees. In multiple embodiments, the included angle φ is between 120 degrees and 160 degrees and the included angle ζ is between 30 degrees and 70 degrees.

In this plane, for a segment from the anterior recess 74 to the articular cartilage surface 77 of the lateral femoral trochlea, this segment 77 may be represented by a circle or an ellipse 80. Although this part appears as ellipses for some subjects, it appears as circles for most subjects. The center 41" of the circle 80 of the plane 72 of the lateral femoral trochlea is completely coincident with the center 41 of the ellipse 40 of the medial femoral trochlea and the center 41' of the most concave plane 62 of the femoral trochlea in the MRI sagittal section. The circle 80 has a radius between 25 mm and 35 mm, such as 28 mm, or 26 mm. An angle between a line for connecting the center 41" of the circle 80 and an intersection point below the ellipse 78 and a line for connecting the center 41" of the circle 80 and the end point of the articular cartilage surface of the lateral femoral trochlea is ρ; and an angle between a line for connecting the center 41 of the circle 80 and the end point of the articular cartilage surface of the lateral femoral trochlea and the horizontal axis is ρ'. The angle ρ is between 80 degrees and 120 degrees, for example, 90 degrees, 100 degrees or 110 degrees; and the angle ρ' is between −30 degrees and 20 degrees, for example, −10 degrees, 0 degrees, or 10 degrees.

Figure 7A:
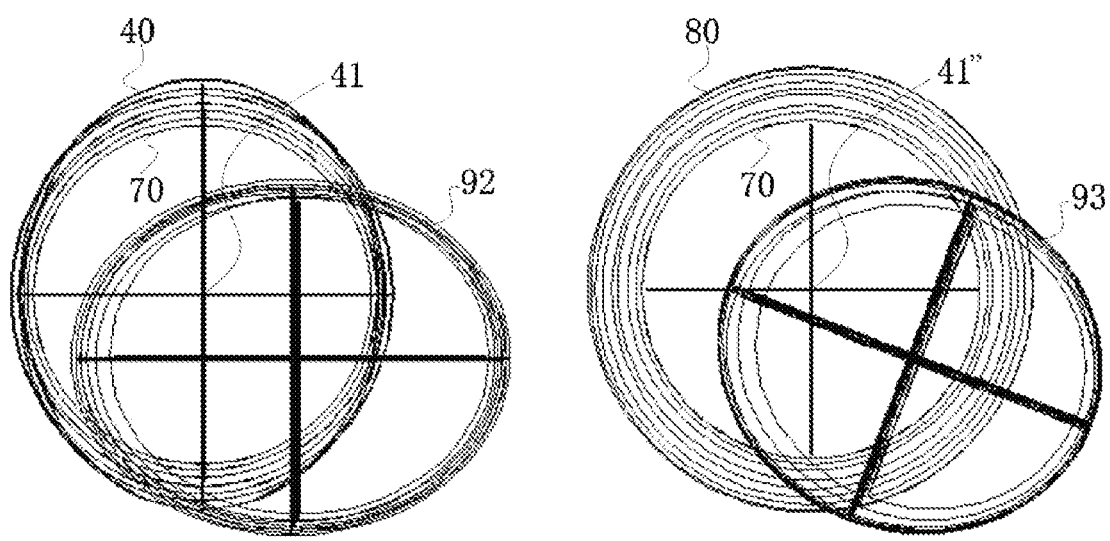
FIG. 7A illustrates a schematic view of an overlap of elliptical configurations and circular configurations of femoral condyles and femoral trochleas of a knee joint of a femoral prosthesis in a sagittal section according to an embodiment of the present disclosure (left is medial side and right is lateral side)

According to an embodiment of the present disclosure, for the femoral condyles, in the MRI sagittal scanning direction, articular cartilage surfaces of the medial femoral condyle and the lateral femoral condyle may almost be represented by ellipses, articular cartilage surfaces of the medial femoral trochlea and the lateral femoral trochlea may almost be represented by ellipses and/or circles, and the most concave portion of the femoral trochlea (i.e., the center of the trochlear groove) is represented by a circle, as shown in FIG. 7A.

Various sagittal planes of an articular cartilage surface of the medial femoral condyle are a set 92 of concentric ellipses, wherein various ellipses have different sizes, major axes and minor axes of the ellipses are in the same direction and are coincident respectively, and various ellipses have similar eccentricities, as shown in FIG. 7A. This represents that a direction in which the medial femoral condyle prosthesis orients the sagittal direction. Therefore, a true direction of the articular cartilage surface of the medial femoral condyle is parallel to the Whiteside line, and is perpendicular to the TEA line. Various sagittal planes of an articular cartilage surface of the lateral femoral condyle are a set 93 of ellipses, as shown in FIG. 7A. Here, various ellipses have different sizes, and major axes and minor axes of the ellipses are in the same direction and are approximately coincident respectively, that is, centers of various ellipses are approximately coincident and are arranged as concentrically. This represents that a direction in which the lateral femoral condyle prosthesis orients the sagittal direction. Therefore, the true direction of the articular cartilage surface of the lateral femoral condyle is parallel to the Whiteside line, and is perpendicular to the TEA line. Various sagittal planes of an articular cartilage surface of the medial femoral trochlea are a set of ellipses (FIG. 7A), major axes and minor axes of the ellipses are in the same direction respectively, and centers of the ellipses are arranged concentrically. However, various ellipses have different eccentricities. Sizes of these ellipses are, for example, ordered in a Fibonacci sequence. The femoral condyle is scanned using the MRI in the sagittal section, and all planes of the lateral femoral trochlea appear as circles or ellipses. Although various circles of the lateral trochlea have different radiuses, or various ellipses of the lateral trochlea have different major and minor axis, projections of the centers 41" thereof are coincident (FIG. 7A).

Figure 7B:
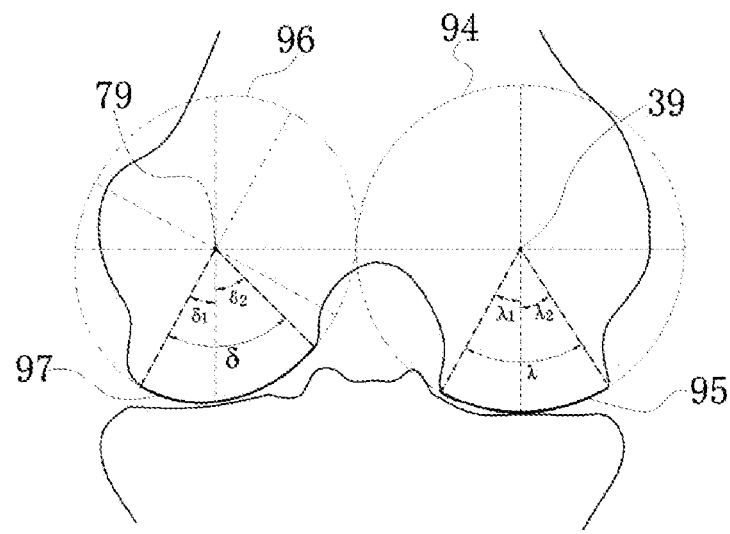
FIG. 7B illustrates a schematic view of an ellipse of a lateral femoral condyle and a circle of a medial femoral condyle 1 in a femoral prosthesis in a coronal plane according to embodiment of the present disclosure.

On a coronal section through the center 39 of the ellipse of the medial femoral condyle and the center 79 of the ellipse of the lateral femoral condyle, the articular surfaces 95, 97 of the medial femoral condyle and the lateral femoral condyle in the coronal section may be represented by a circle and an ellipse, as shown in FIG. 7B. With the center 39 of the ellipse of the medial femoral condyle as a center, a circle 94 (the sixth circle) can well fit the articular surface 95 of the medial femoral condyle in the coronal section, and a radius of the circle 94 is equal to the semi-minor axis of the ellipse 38 of the medial femoral condyle. An arc angle of the articular surface in this segment may be represented by an angle λ, for example, the arc angle ranges from 50 degrees to 90 degrees. λ is divided by a vertical line into λ1 and λ2, wherein λ1 and λ2 may or may not be equal. In one embodiment, the angle A is 65 degrees; and in another embodiment, the angle λ is 70 degrees. With the center 79 of the ellipse of the lateral femoral condyle as a center, an ellipse 96 (the seventh ellipse) is rotated clockwise by δy degrees, is then just tangent to the medial circle 94 (the sixth circle) and best-fit the articular surface 97 of the lateral femoral condyle in the coronal section. If the ellipse 96 has an eccentricity of 0.618, it is a perfect ellipse. An arc angle of the articular surface in this segment may be represented by an angle δ, for example, the arc angle ranges from 50 degrees to 90 degrees. δ is divided by a vertical line into δ1 and δ2, wherein δ1 and δ2 are not equal. In one embodiment, the angle δ is 70 degrees; and in another embodiment, the angle δ is 75 degrees.

Figure 8:
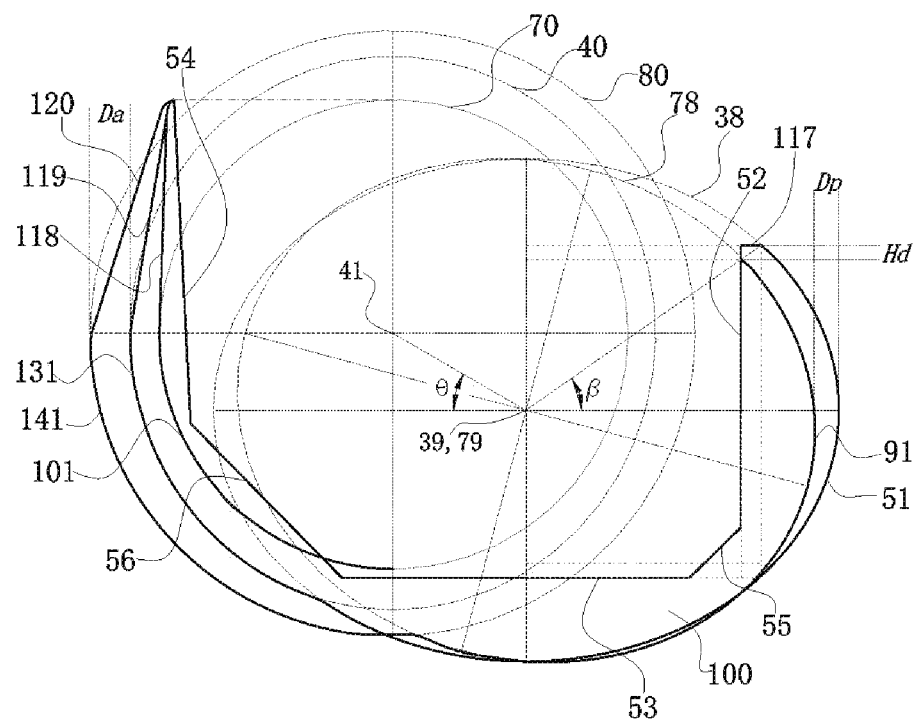
FIG. 8 illustrates a schematic cross-sectional view of a femoral prosthesis in a sagittal section (medial and lateral overlap) according to the present disclosure, illustrating a relationship among various ellipses and circles, and features and geometrical structures of the ellipses and the circles.

The femoral prosthesis according to the embodiments of the present disclosure has sagittal posterior condyles in an elliptical geometry, and sagittal trochleas in an elliptical and/or a circular geometry, wherein the lateral posterior condyle is shorter than and lower than the medial posterior condyle, and the lateral trochlea is longer than and higher than the medial trochlea. According to the above embodiments, it is known that the center 39 of the ellipse 38 of the medial femoral condyle coincides with the center 79 of the ellipse 78 of the lateral femoral condyle, and the center 41 of the ellipse 40 of the medial femoral trochlea, the center 41' of the circle 80 of the lateral femoral trochlea, and the center 41" of the circle 70 at the most concave portion of the femoral trochlea are coincident. Therefore, a sagittal shape of the TKA femoral prosthesis 100 according to the embodiments of the present disclosure is as shown in FIG. 8. The femoral prosthesis 100 according to the present disclosure is divided into articular surface portions, that is, an outside surface of the prosthesis which is in contact with the patella and the tibia plateau during the motion of the knee joint; and an inside portion, that is, a portion which is adjacent to an osteotomy surface of the femoral condyle and a bone cement after the femoral prosthesis is implanted. The sagittal articular surface of the femoral prosthesis 100 is designed to be asymmetric. Anteroposterior diameters and heights of the sagittal articular surface of the femoral prosthesis 100 are determined by parameters of five basic elements 38 (the ellipse of the medial femoral condyle), 40 (the ellipse of the medial femoral trochlea), 70 (the circle of the most concave trochlear groove), 78 (the ellipse of the lateral femoral condyle), 80 (the circle or ellipse of the lateral femoral trochlea) which form the articular surface and the angles θ and β. For convenience of description, the femoral prosthesis 100 may be divided into medial elements which are a half of elements of the femoral prosthesis, i.e., including a medial condyle portion 51 of the femoral prosthesis and a medial trochlear portion 131 of the femoral prosthesis; lateral elements which are a half of the elements of the femoral prosthesis, i.e., including a lateral condyle portion 91 of the femoral prosthesis and a lateral trochlear portion 141 of the femoral prosthesis; and a trochlear groove 101 of the femoral prosthesis, i.e., a position where the most concave plane of the trochlea is located. In the sagittal section, the articular surface geometry of the medial elements 51, 131 which are a half of the elements of the femoral prosthesis is composed of an ellipse 38 and an ellipse 40; the articular surface geometry of the lateral elements 91,141 which are a half of the elements of the femoral prosthesis is composed of an ellipse 78 and a circle or ellipse 80; and the articular surface geometry of the trochlear groove 101 of the femoral prosthesis is composed of a circle 70.

The geometric shape of the articular surface of the femoral prosthesis is asymmetric, with the lateral portion of the femoral prosthesis being forwardly spaced relative to the medial portion of the femoral prosthesis. Therefore, the posterior offset of the lateral condyle 91 of the femoral prosthesis is less than that of the medial condyle 51 and the posterior height of the lateral condyle 91 is lower than that of the medial condyle 51. The anterior offset of the lateral trochlea 141 of the femoral prosthesis is greater than that of the medial trochlea 131. In the axial section, the femoral prosthesis has its own external rotation. In conclusion, it should be protected that the posterior lateral condyle of the femoral prosthesis is shorter and lower than that of the posterior medial condyle of the femoral prosthesis. This design feature is beneficial to increase a flexion angle of the knee joint. In addition, the anterioposterior diameters and heights of the articular surfaces of the femoral prosthesis may be accurately calculated using the parameters of ellipses and circles which form the femoral prosthesis, and the important angle values. The parameter values of the femoral prosthesis thereof vary accordingly with the prosthetic sizes.

In the sagittal section, the lateral elements 91, 141 which are a half of the elements of the femoral prosthesis are forwardly spaced relative to the medial members 51, 131 which are a half of elements of the femoral prosthesis. This forward distance has different parameter values depending on the prosthetic sizes, for example, 1 mm, 2 mm, 3 mm, or 4 mm. In detail, the posterior portion of the lateral condyle 91 of the femoral prosthesis is shorter than and lower than the posterior portion of the medial condyle 51 of the femoral prosthesis. This forms a distance difference Dp, and a height difference Hd, as shown in FIG. 8. The parameter values of Dp and Hd are not fixed values, which vary with the prosthetic sizes, that is, they vary with the parameter values of the ellipses 38, 40, 78 and the circles or ellipse 70, 80 which form the articular surface. For example, the value of Dp may be 2 mm, 3 mm, or 4 mm; and the value of Hd may be 1 mm, 2 mm, or 3 mm. The posterior end of the medial condyle 51 of the femoral prosthesis is more flat and blunt 117 than that of the posterior end of the lateral condyle 91 of the femoral prosthesis. Parameter values of this flat blunt surface 117 also vary with the prosthetic sizes. An anterior edge of the lateral trochlear portion 141 of the femoral prosthesis is more forward in the sagittal section, and is higher in the axial section than an anterior edge of the medial trochlear portion 131 of the femoral prosthesis, as in FIG. 9A. This forms a distance difference Da therebetween. A value of Da is not fixed, and varies with the parameters of the ellipses 38, 40, 78 and the circles and ellipse 70, 80 which form the articular surface. For example, the value of Da may be 2 mm, 3 mm, 4 mm, or 5 mm. Anterosuperior portions (flange) 118, 119, 120 of an the femoral prosthesis 100 are tangent to an anterior bone cortex of a femoral shaft, and are designed to have a short linear shape to reduce a pressure on the patella, wherein the vertex of the anterosuperior portions (flange) is in the same level as the vertex of the circle 70 at the most concave portion of the femoral trochlea.

The inside structure of the femoral prosthesis is symmetrical to facilitate the osteotomy step and the gap balancing step. The parameter values of the inside structure that corresponding to the osteotomy line thereof may be accurately calculated using the ellipses and the circles which form the femoral prosthesis, and important angle values. The parameter values thereof vary accordingly with the prosthetic sizes.

The inside structure 52, 53, 54, 55, 56 of the femoral prosthesis 100 have a rectangular structure (with/without bone cement) which is in contact with the distal femur after osteotomy. In order to simplify the osteotomy step and facilitate intraoperative gap balancing techniques, the inside structure of the femoral prosthesis 100 are designed to be a symmetrical rectangle. The posterior section 52 of the inside sides of the femoral prosthesis is perpendicular to the horizontal axis, i.e., being perpendicular to the major axis of the medial ellipse 38 of the medial femoral condyle, as shown in FIG. 8. The posterior section 52 according to the present disclosure can be cut just to the end position of the articular surface of the medial and lateral femoral condyles 42, 82, as shown in FIG. 4B. Further, the parameter values of the position and height of the posterior section 52 of the medial sides of the femoral prosthesis may be determined through the medial ellipse 38 of the medial femoral condyle. A line for connecting the end point of the articular surface of the posterior condyle of the medial condyle portion 51 of the femoral prostheses and the center 39 of the medial ellipse 38 of the medial femoral condyle passes through the end point of the condyle articular surface of the lateral condyle portion 91 of the femoral prosthesis. An angle between the line and the major axis of the medial ellipse 38 of the medial femoral condyle is β. Therefore, the position and height of the posterior section 52 of the inside sides of the femoral prosthesis may be calculated according to the basic formula of the ellipse. The position and height of the posterior section 52 vary with the prosthetic sizes. The parameter values of the inferior section 53 and the posterior slope section 55 of the inside sides of the femoral prosthesis are directly affected by the posterior section 52; and the end point of the articular surface of the posterior condyle of the medial femoral condyle portion 51 is located in a rectangular frame formed by the major axis and the minor axis of the medial ellipse 38 of the femur; and parameter values thereof vary with the prosthetic sizes. The anterior section 54 of the inside sides of the femoral prosthesis 100 moves back by a thickness of one cartilage surface relative to the trochlear groove 101 of the femoral prosthesis to ensure removal of the cartilage surface at the most concave portion of the trochlea, for example 2 mm or 3 mm. At the same time, it has an anteversion angle of 2 degrees relative to the mechanical axis or the minor axis of the medial ellipse 38 to prevent notch to the anterior bone cortex at the distal end of the femur, and the anteversion angle may also be 1 or 3 degrees. A segment from the end of the inferior section 53 of the inside sides intersects with the anterior section 54 of the inside sides at an angle of 45 degrees relative to the major axis of the medial ellipse 38, to form an anterior slope section 56 of the inside sides. Accordingly, parameters of the anterior section 54 and the anterior slope section 56 of the inside sides of the femoral prosthesis are determined by the parameters of the medial and lateral femoral ellipses 38, 78, the ellipse 40 of the femoral trochlea, and the circles or ellipse 70, 80 of the femoral trochlea, and the angles θ and β. The trochlear groove 101 of the femoral prosthesis is designed as a ¼ arc, and its specific parameter values (depth and radius) are directly determined by the circle 70 in the most concave plane of the trochlea, the medial femoral ellipse 38, and the angle θ, and vary with the prosthetic sizes.

The femoral prosthesis 100 according to the present disclosure is viewed from the perspective of an axial section, as shown in FIG. 9A. The medial trochlear portion 131 of the femoral prosthesis, the lateral condyle portion 91 of the femoral prosthesis, the lateral trochlear portion 141 of the femoral prosthesis, and the trochlear groove 101 of the femoral prosthesis are designed to be perpendicular to a line 133 for connecting the centers 39, 79 of the ellipses of the medial femoral condyle and the lateral femoral condyle (TEA direction). Here, the center 39 of the medial ellipse 38 corresponds to the vertex of the medial femoral condyle in the axial section, in other words, the attachment point of the medial collateral ligament 123; and the center 79 of the lateral femoral ellipse 78 corresponds to the vertex of the lateral femoral condyle in the axial section, in other words, the attachment point of the lateral collateral ligament 122. The anterior offset of the articular surface of the lateral femoral trochlea is greater than that of the articular surface of the medial femoral trochlea, with a distance therebetween of Da described above; the posterior offset of the lateral condyle 91 of the femoral prosthesis is less than that of the medial condyle 51, with a difference therebetween of Dp described above; and an angle between a line for connecting the lateral posterior condyle and the medial posterior condyle and the TEA is π, for example, the angle π may be 3 degrees, 2 degrees or 4 degrees, etc.

According to the above ellipse and circle principle in the sagittal section, and the ellipse and circle principle in the coronal section, in a non-patella arthroplasty-type prosthesis, the medial femoral condyle has a circular arc structure in the coronal section; and the lateral femoral condyle has an elliptical arc structure in the coronal section. The tibial plateau side has a corresponding asymmetric structure. Further, the tibial plateau side is modified to adapt to a varus angle of the mechanical axis of the lower extremity. Maybe in a prosthesis with patella arthroplasty, the medial femoral condyle and the lateral femoral condyle have a symmetrical circular arc structure in the coronal section.

Figure 9B:
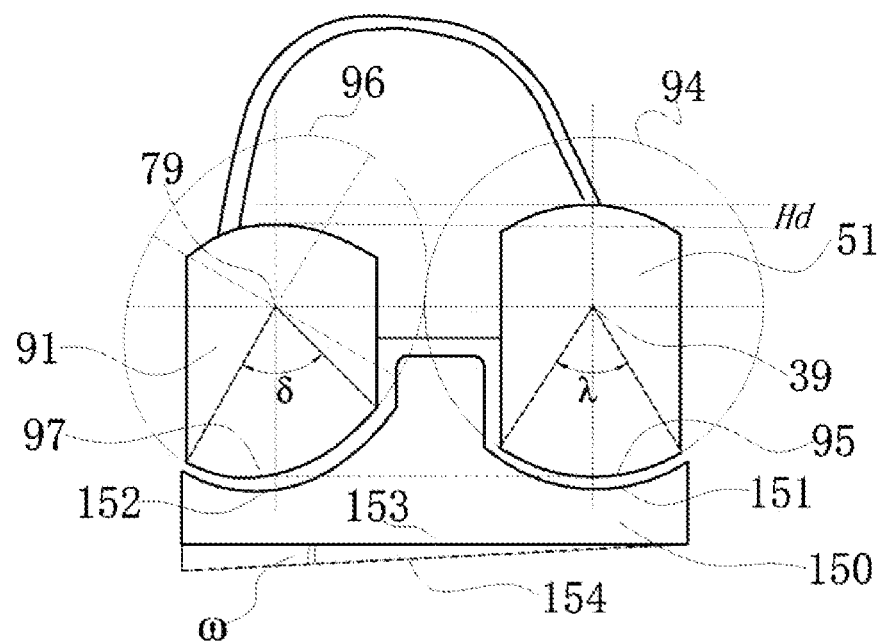
FIG. 9B illustrates a rear view of a femoral prosthesis in a coronal section according to the present disclosure, illustrating shapes of a medial femoral condyle and a lateral femoral condyle in the coronal section and a structure of corresponding plateau portions with non-patella arthroplasty.

A posterior viewing of the femoral prosthesis 100 according to the present disclosure in the coronal section is as shown in FIG. 9B. The lateral condyle 91 of the femoral prosthesis is lower than the medial condyle 51 of the femoral prosthesis, with a difference therebetween of Hd described above. According to the ethnic and intraoperative specific conditions, design of the contour of the articular surfaces of the medial femoral condyle and the lateral femoral condyle in the coronal section and the femoral trochlear groove 101 may be divided into two types: a non-patella arthroplasty type and a patella arthroplasty type. When arthroplasty of a patient's patella does not occur, the articular surfaces of the medial condyle and the lateral condyle of the femoral prosthesis 100 in the coronal section are designed to be arcs of a circle and an ellipse, as shown in FIGS. 7B and 9B. The articular surface 95 of the medial condyle of the femoral prosthesis in the coronal section is an arc of a circle 94, which is represented by an angle λ. The center of the circle 94 is the center 39 of the ellipse 38 of the medial femoral condyle and has a radius equal to the semi-minor axis of the ellipse 38 of the medial femoral condyle. A coronal surface 151 of the medial plateau of the plateau prosthesis 150 corresponding to the articular surface 95 has a concavo shape which fully adapts to the curvature of the articular surface 95. The articular surface 97 of the lateral condyle of the femoral prosthesis in the coronal section is an arc of an ellipse 96, which is represented by an angle δ The center of the ellipse 96 is the center 79 of the ellipse 78 of the lateral femoral condyle having an eccentricity of 0.618 and a radius approximately equal to the semi-minor axis of the ellipse 38 of the medial femoral condyle. A coronal surface 152 of the lateral plateau of the plateau prosthesis 150 corresponding to the articular surface 97 has a concave structure which fully adapts to the ellipse of the articular surface 97. Therefore, the coronal structure of the tibial plateau prosthesis 150 corresponding to the non-patella arthroplasty-type femoral prosthesis is as described above. The distal end surface 154 of the tibial plateau prosthesis 150 may be designed to be perpendicular to a mechanical axis of the tibia or has a varus angle ω, so as to adapt to the varus of the normal tibial plateau related to the mechanical axis of lower extremity. (i.e., kinematic alignment). The angle ω may be 1 degree, 2 degrees or 3 degrees. The trochlear groove 101 is designed with reference to the medial femoral trochlea and the lateral femoral trochlea in the sagittal section which are composed of ellipses and circles 40, 70, 80, as shown in FIG. 7A. When arthroplasty of a patient's patella occurs, the articular surface of the lateral condyle in the coronal section is designed to be an arc of a circle; and the trochlear groove is designed to be a groove with a valgus angle of 6°, to correspond to a dome shape of the patella prosthesis.

After appropriate intercondylar adjustment, the femoral prosthesis constructed according to the above ellipse principle may be adapted for the production of a CR prosthesis and/or a PS prosthesis.

According to the above ellipse principle, after appropriate adjustment, it may be applied to the design and manufacturing of an UKA prosthesis, and/or the design and manufacturing of a trochlear portion arthroplasty prosthesis, and/or the manufacturing of an assembly-type femoral prosthesis.

According to the above embodiments, the medial and lateral condyles of the femoral prosthesis are arcs of ellipses in the sagittal section. The major axes of the medial condyle ellipses are perpendicular to the diaphyseal axis of the femur, and the major axes of the lateral condyle ellipses may be rotated clockwise by a certain angle (7 degrees to 22 degrees) relative to the major axis of the ellipse of the medial condyle. According to some embodiments, shapes of both of the medial and lateral femoral condyles may be represented by ellipses on the sagittal scanning plane. This can enable explanation of accurate spatial positions of the TEA, the derivation and value of the posterior offset of the femoral condyles and the reason of the posterior slope the tibial plateau. According to some embodiments, the articular surface of the medial femoral trochlea is an arc of an ellipse in the sagittal section, and the ellipse has a major axis perpendicular to the major axis of the medial ellipse. The articular surface of the lateral femoral trochlea in the sagittal section is an arc of a circle or an ellipse. The prosthesis according to the above embodiments has a geometry closest to that of a distal femur of a normal human body, which helps to better design the TKA femoral prosthesis and greatly simplifies the design parameter values of various prosthetic sizes.

According to an embodiment of the present disclosure, the ellipse of the medial femoral condyle is designed to have a concentric elliptical structure perpendicular to the TEA and parallel to the Whiteside line in the sagittal plane, which is most consistent with the direction and geometric shape of a medial femoral condyle in a normal human body. The ellipse of the lateral femoral condyle is designed according to a shape of an articular cartilage surface of a lateral femoral condyle of a normal knee. The ellipse of the lateral femoral condyle is slightly less than the ellipse of the medial femoral condyle. A major axis direction of the lateral femoral condyle is rotated clockwise by a certain angle relative to the ellipse of the medial femoral condyle. At the same time, centers of the ellipses of the medial and lateral femoral condyles coincide in the sagittal section of the femoral prosthesis. However, in an alternative plan, the major and minor axis of the lateral femoral condyle ellipse may be simplified to have the same directions as those of the medial femoral condyle. The clockwise rotation may be omitted, which further simplifies the design and manufacturing process of the femoral prosthesis. Although the shape after the change is not coincident with the normal shape of an articular cartilage surface of a lateral posterior femoral condyle, it is also feasible. A good joint kinematics can also be obtained with adjustment of polyethylene tray of the tibial side.

Furthermore, in the above embodiment, the medial and lateral femoral trochleas are described as being composed of an ellipse or circle. This plan is obtained by a final statistical analysis. Although the medial femoral trochlea according to most of the embodiments appears as ellipses, there are a few embodiments in which the medial femoral trochlea appears as circles; and although the lateral femoral trochlea according to most of the embodiments appears as circles, there are a few embodiments in which the lateral femoral trochlea appears as ellipses.

It should be clarified that the principle of the features of the femoral prosthesis described here is equally and same applicable to left knee joint or right knee joint. It should be clarified that the design of the femoral prosthesis according to the present disclosure comprises a CR prosthesis, a PS prosthesis or other revision prosthesis designs. The CR prosthesis, relative to the PS prosthesis, omits a cam structure on the elements of the femoral prosthesis and a post structure on elements of the tibial prosthesis. This allows the CR prosthesis to appear between the lateral condyle and the medial condyle as an intercondyal space with an open box structure. Any types of prostheses may be formed by suitably modifying the femoral prosthesis according to the present disclosure to add the cam structure on the elements of the femoral prosthesis and the post structure on the tibial side. Therefore, all of the principles described in the present disclosure may be used to design any potentially knee prosthesis. Although any potentially contemplated knee prosthesis design may comprise all of the features described here, it is also contemplated that some potentially contemplated knee prosthesis designs may omit or may be added with some of the features described here, depending on particular applications or requirements in other situations.

In some special cases, for example, during the production of an UKA prosthesis (an unicompartmental medial condyle prosthesis and/or an unicompartmental lateral condyle prosthesis) and/or a trochlear prosthesis, and a prosthesis formed by assembling them, these cases are still protected by the present patent.

Figure 10:
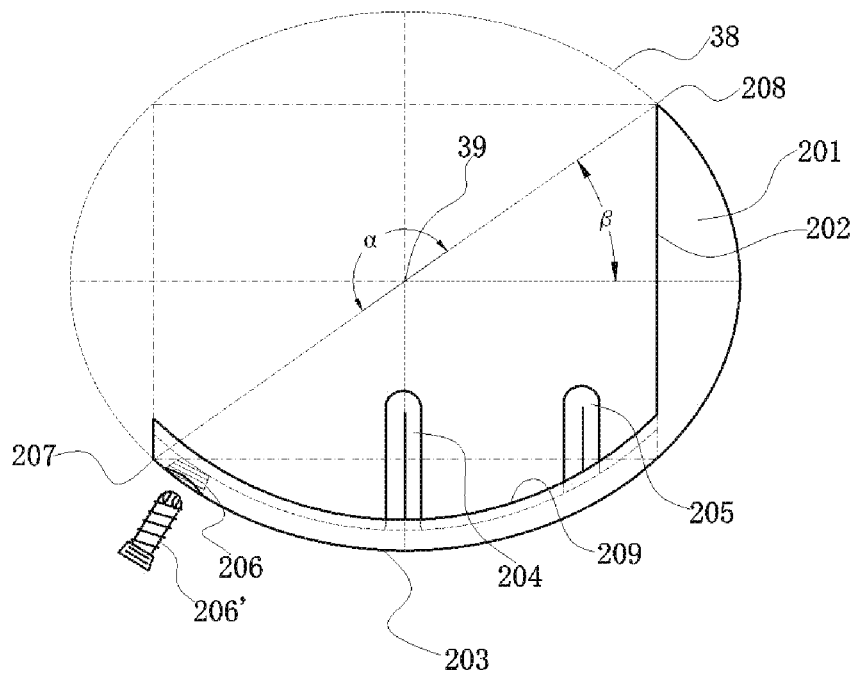
FIG. 10 illustrates a schematic cross-sectional view of an UKA prosthesis of a medial femoral condyle in a sagittal section according to an embodiment of the present disclosure.
Figure 11:
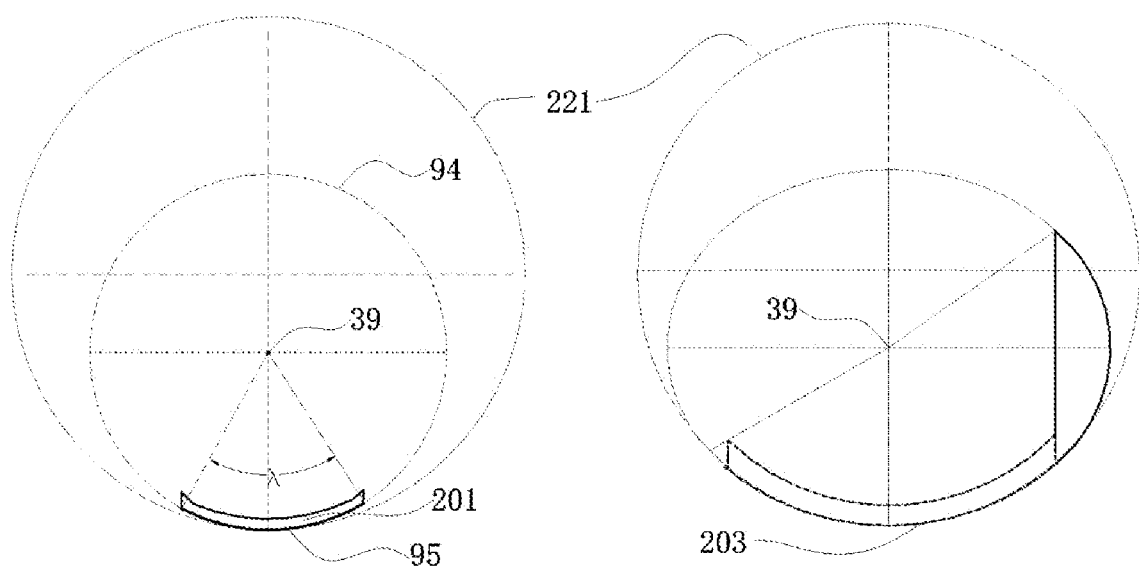
FIG. 11 illustrates a schematic cross-sectional view of an UKA prosthesis of a medial femoral condyle in a coronal section according to an embodiment of the present disclosure.

The UKA prosthesis of the medial femoral condyle according to the embodiments of the present disclosure has an elliptical geometry in the sagittal section and a circular geometry in the coronal section. According to the above embodiments, it is known that the medial femoral condyle is a set of concentric ellipses, and these elliptical planes are spatially parallel to the Whiteside line of the trochlea. Centers of these ellipses correspond to the attachment point of the medial collateral ligament of the medial femoral condyle. Therefore, the geometry of the UKA prosthesis of the medial femoral condyle is composed of concentric ellipses in the sagittal section, as shown in FIG. 10; and is composed of circles in the coronal section, as shown in FIG. 11. The UKA prosthesis 201 of the medial femoral condyle according to the present disclosure is divided into an articular surface portion, that is, an outside surface of the prosthesis which is in contact with a medial patella and a medial tibial plateau during motion of a knee joint; and an inside side portion, that is, a portion adjacent to an osteotomy surface of a femoral condyle portion and a bone cement after the UKA prosthesis 201 of the medial femoral condyle is placed, wherein the inside side portion appears as a posterior condyle of the inside side in a straight section, and a distal portion in the inside side conformal to the arc of the articular surface.

In the sagittal section, the UKA prosthesis 201 of the medial femoral condyle is an arc 203 of an ellipse 38, as shown in FIG. 10. Anterior and posterior edges of the arc 203 correspond to the recesses of the anterior and posterior meniscus, and form an arc angle α range of, for example, 150 degrees to 200 degrees, wherein the arc angle α range is 175 degrees in one embodiment, and 185 degrees in another embodiment, and 180 degrees in yet another embodiment. Specifically, it may be expressed as an angle δ between a straight line for connecting anterior and posterior recesses 207, 208 of the meniscus and passing through the center 39 of the ellipse of the medial femoral condyle and the major axis of this ellipse. This angle δ is 30 degrees in one embodiment, 35 degrees in another embodiment, and 40 degrees in yet another embodiment. The posterior section 202 of the inside side of the UKA prosthesis of the medial femoral condyle is a line orienting the posterior recess 208 of the meniscus which is perpendicular to the major axis of the ellipse, and corresponding the osteotomy on the posterior condyle. This position changes with the parameters of the prosthesis change. The distal portion 203 of the UKA prosthesis 201 of the medial femoral condyle has an elliptical arc configuration. The inside side thereof has two pillars, which are a central pillar 204 corresponding to the center 39 of the ellipse of the medial femoral condyle, and a posterior pillar 205 corresponding to the focus of this ellipse, respectively. At the anterior edge of the distal portion component 203 of the UKA prosthesis, there is also a locking screw hole 206 for locking a screw to correspond to a locking screw 206'. In a case of a normal human body, this position contacts the meniscus and neither contacts the articular surface of the tibial plateau, nor contacts the patella. Therefore, screw fixation at this position does not affect the articular surface. Moreover, a direction in which the fixing screw 206' is locked is different from that of the central pillar and the posterior pillar, and the stability of the prosthesis can be enhanced. It can be understood that those skilled in the art can provide a greater number of pillars as desired.

In the coronal section, it can be known according to FIG. 5 that, the shape of the articular surface of the medial femoral condyle in the coronal section may be represented by an arc 95 of a circle 94, which has an arc angle of λ, for example, a range of the arc angle is from 50 degrees to 90 degrees. Therefore, the shape of the UKA prosthesis 201 of the medial condyle in the coronal section is as shown in FIG. 11. In the sagittal section, an arc 203 may be seen as being approximately coincident with a circle 221 having a radius greater than that of the circle 94 of the UKA prosthesis 201 in the coronal section. A curvature and parameters of this circle 221 are used as parameters of an abrasive tool to prepare a bone bed surface.

Figure 12:
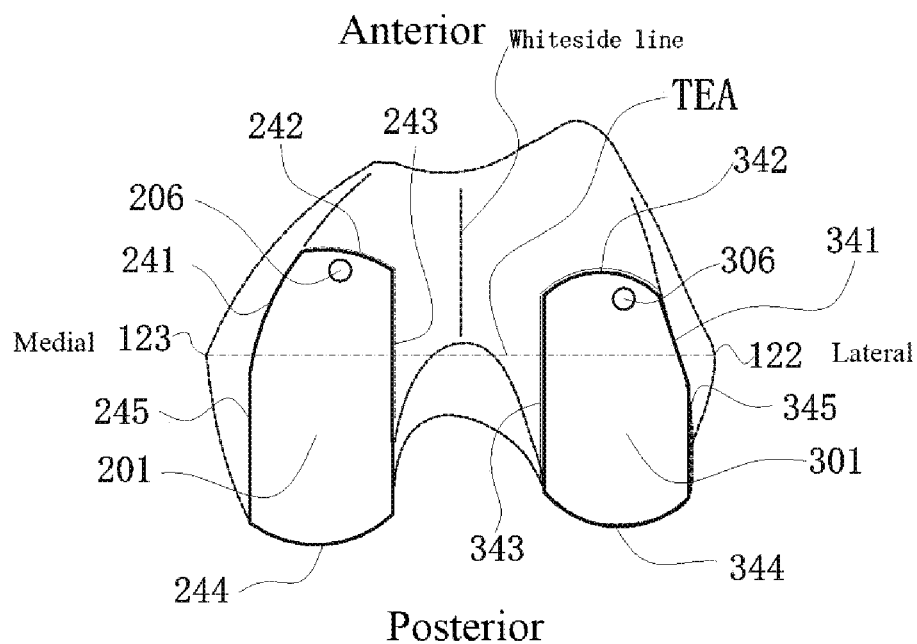
FIG. 12 illustrates a schematic view of an UKA prosthesis of a medial femoral condyle and a lateral femoral condyle in an axial section according to an embodiment of the present disclosure.
Figure 13:
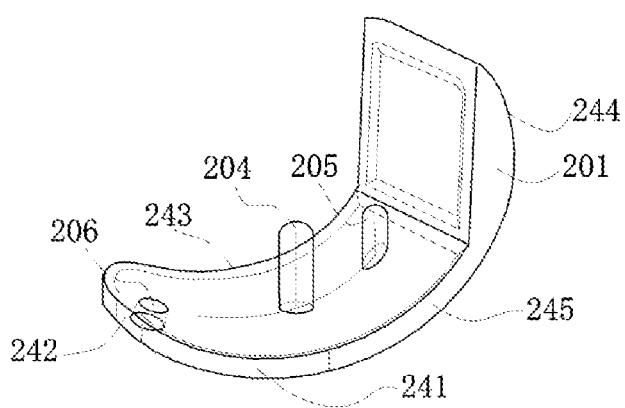
FIG. 13 is a stereogram illustrating an UKA prosthesis of a medial femoral condyle according to an embodiment of the present disclosure.

From the perspective of an axial section, the articular surface of the UKA prosthesis 201 of the medial femoral condyle is asymmetrical, as shown in FIG. 12. The prosthesis is placed to be parallel to the Whiteside line and perpendicular to the TEA. There are straight edges 243, 245 on medial and lateral sides of the prosthesis respectively, and the straight edges 243, 245 are parallel to the Whiteside line and perpendicular to the TEA. A medial arc edge 241 is arc-shaped to adapt to the shape of the distal shape of the medial femoral condyle; an anterior arc edge 242 has a curvature corresponding to parameters of a circle 221 of an abrasive tool, and a posterior portion 244 has a curvature of the circle 94 in the coronal section. Therefore, a stereogram of the UKA prosthesis 201 of the medial femoral condyle is shown in FIG. 13. In addition to various positions described above, the inside sides of the prosthesis have corresponding concave grooves to adapt to the bone cement.

Figure 14A:
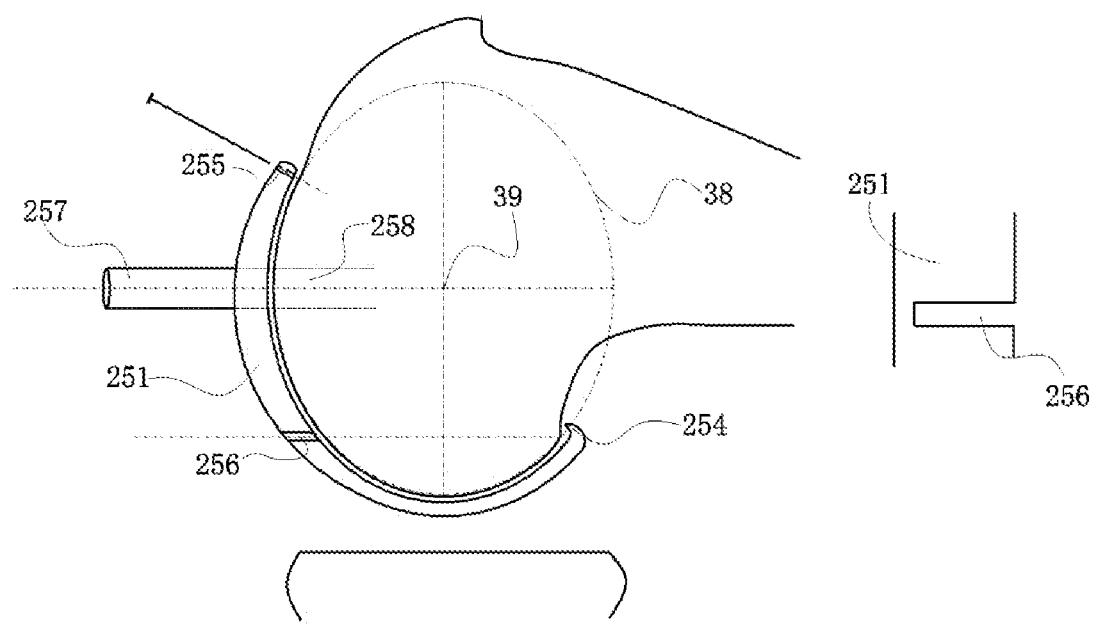
FIG. 14A is a schematic view illustrating an operation of placing an UKA prosthesis of a medial femoral condyle and use of corresponding instruments according to an embodiment of the present disclosure.
Figure 14B:
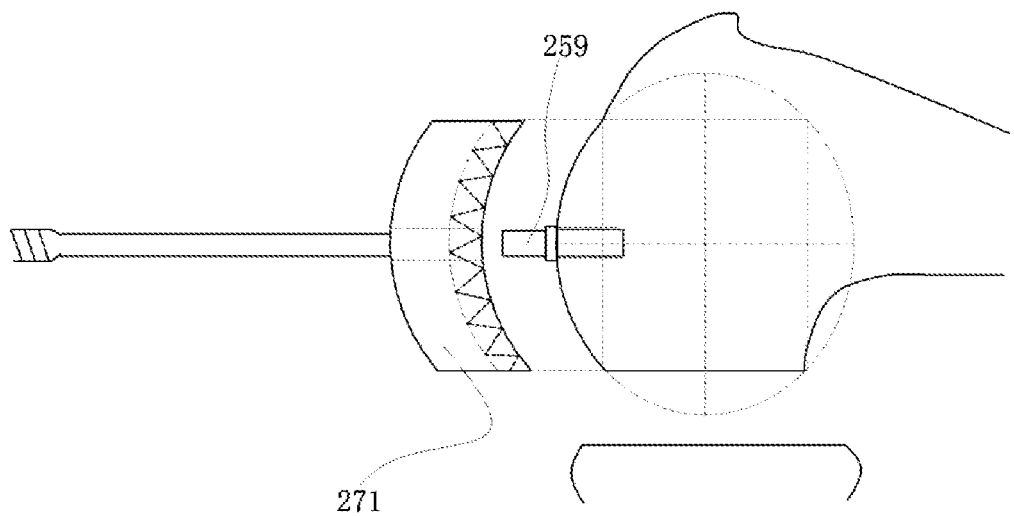
FIG. 14B is a schematic view illustrating an operation of placing an UKA prosthesis of a medial femoral condyle and use of corresponding instruments according to an embodiment of the present disclosure.

Best size and position of the prosthesis may be planned on a preoperative MRI scanning on the femoral condyle as described above. A specific surgical operation comprises: after exposure, firstly determining the Whiteside line of the trochlear groove, and marking a direction line of the prosthesis which is parallel to the Whiteside line on the medial condyle surface using an electric knife. An ellipse measuring tool 251, which is most compatible with the ellipse of the medial femoral condyle, fits well to the articular surface, as shown in FIG. 14A. An anterior edge of the measuring tool 251 has a grapple structure 254 which can hold the medial posterior condyle well. There are two screw holes 255 at the end of the measuring tool 251, and the two screw holes 255 are fixed using short screws for greater stability. It must be ensured that a hollow handrail 257 of the measuring tool 251 is right against the direction of the attachment point of the medial collateral ligament, i.e., the direction of the center 39 of the ellipse of the medial femoral condyle. The hollow handrail 257 may have a drill bit placed therein, to drill a tunnel 258 in the medial femoral condyle to facilitate the next step of placing a fixed pile at the center of the power drill. There is an osteotomy groove 256 at the bottom of the measuring tool 251, and the osteotomy groove 256 is right against a posterior osteotomy line 202 of the medial femoral condyle. As shown in FIG. 14B, the measuring tool 251 is then removed, the fixed pile 259 is placed on the central tunnel 258, and a hollow drill 271 is used, which has a radius equal to that of the circle 221 described above. A depth of a rasion is limited by the fixed pile 259, and the prosthesis is continuously tested for the depth during this period.

The UKA prosthesis of the lateral femoral condyle according to the embodiments of the present disclosure has an elliptical geometry in both the sagittal section and the coronal section. According to the above embodiment, it is known that the lateral femoral condyle is a set of concentric ellipses, and these ellipses are spatially parallel to the Whiteside line of the trochlea. Centers of these ellipses correspond to the attachment point of the lateral collateral ligament of the lateral femoral condyle. Therefore, the geometry of the UKA prosthesis of the lateral femoral condyle is composed of concentric ellipses in the sagittal section and ellipses in the coronal section, as shown in FIG. 10. The UKA prosthesis 301 of the lateral femoral condyle according to the present disclosure is divided into an articular surface portion, that is, an outside surface of the prosthesis which is in contact with the lateral patella and the lateral tibial plateau during the motion of the knee joint; and an inside side portion, that is, a portion adjacent to an osteotomy surface of a femoral condyle portion and a bone cement after the UKA prosthesis 301 of the lateral femoral condyle is placed, wherein the inside side portion appears as a posterior condyle of the inside side in a straight section, and a distal portion of the inside side conformal to the arc of the articular surface.

Figure 15:
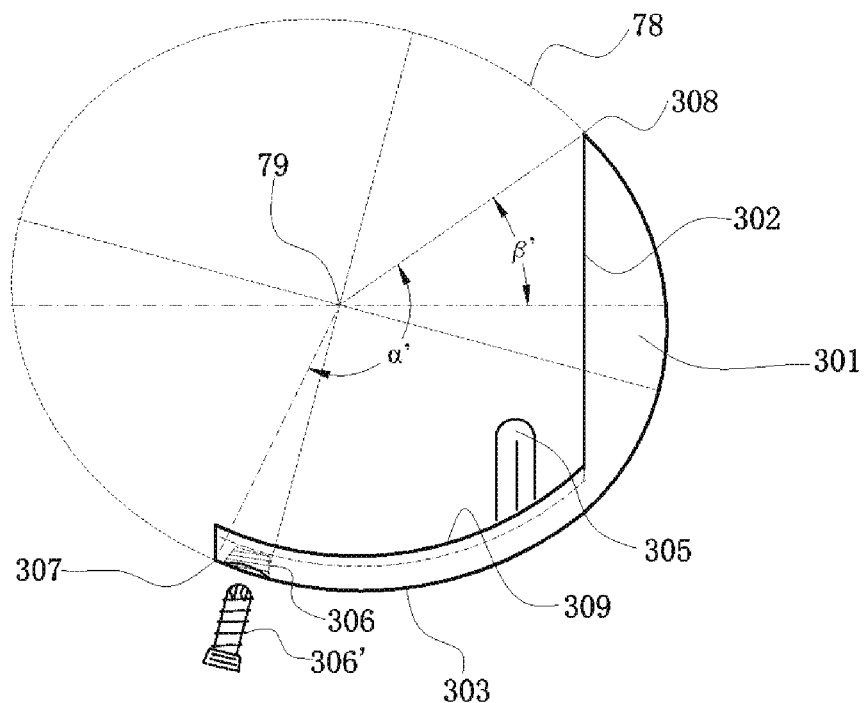
FIG. 15 is a schematic cross-sectional view illustrating an UKA prosthesis of a lateral femoral condyle in a sagittal section according to an embodiment of the present disclosure.

In the sagittal section, the UKA prosthesis 301 of the lateral femoral condyle is an arc of an ellipse 78, as shown in FIG. 15. The anterior and posterior edges of the arc correspond to the recesses 307, 308 of the anterior and posterior meniscus, and form an arc angle range, for example, the arc angle range is from 120 degrees to 160 degrees. In one embodiment, the arc angle is 145 degrees, and in another embodiment, the arc angle is 150 degrees. Specifically, it may be expressed as an angle α' between the anterior and posterior recesses 307, 308 of the meniscus and the center 79 of the ellipse of the lateral femoral condyle. An angle between a line for connecting the center 79 and the posterior recess 308 of the meniscus and the horizontal axis is β', which is 35 degrees in one embodiment, 40 degrees in another embodiment, and an average of 35 degrees in multiple embodiments. The posterior section 302 of the inside side that is corresponding to the osteotomy direction of the UKA prosthesis 301 of the lateral femoral condyle is perpendicular to the horizontal axis. This position changes as the parameters of the ellipse change. The distal portion 303 of the UKA prosthesis 301 of the lateral femoral condyle has an elliptical arc configuration. There is a pillar on the inside side, that is, a posterior pillar 305 corresponding to the focus of the ellipse. There is also a locking screw hole 306 at the anterior edge of component 303, to correspond to a locking screw 306'. In a case of a normal human body, this position contacts the meniscus and does not contact the articular surface of the tibial plateau; and at the same time, the position of the screw hole does not contact the patella. Therefore, screw fixation at this position does not affect the contact of the articular surface. Moreover, a direction in which the fixing screw 306' is locked is different from that of the posterior pillar, and the stability of the prosthesis can be enhanced.

Figure 16:
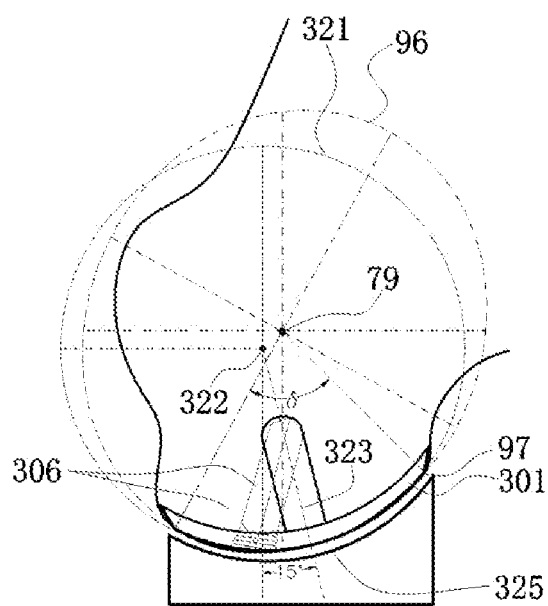
FIG. 16 is a schematic cross-sectional view illustrating an UKA prosthesis of a lateral femoral condyle in a coronal section according to an embodiment of the present disclosure.

In the coronal section, it can be known according to FIG. 5 that, the shape of the articular surface of the lateral femoral condyle which passes through the center 79 may be represented by an arc 97 of an ellipse 96, which has an arc angle of δ, for example, a range of the arc angle is from 50 degrees to 90 degrees. Therefore, the shape of the UKA prosthesis 301 of the lateral condyle in the coronal section is shown in FIG. 16, and a shape of an articular surface of a corresponding tibial prosthesis in the coronal section is a concave shape 325 adapted to this ellipse. This arc 97 may approximately coincide with a circle 321 which does not pass through the center 79. The center is 322 of the circle 321, and a radius of the circle 321 may be regarded to be equal to a length of the semi-minor axis of the ellipse 96. The direction axis 323 is not only the direction of the posterior pillar 305, but also a direction of a burr drill and the fixed pile. An angle between the direction axis 323 and the vertical axis is 15 degrees. The curvature and parameters of the circle 321 are used as the parameters of the abrasive tool to prepare the bone bed surface. In the coronal section, an angle between a direction of the locking screw holes and the locking screw 306 and the vertical axis is 15 degrees. Therefore, an angle between the locking screw 306 and the posterior pillar 305 is 30 degrees to achieve maximum stability of the prosthesis.

Figure 17:
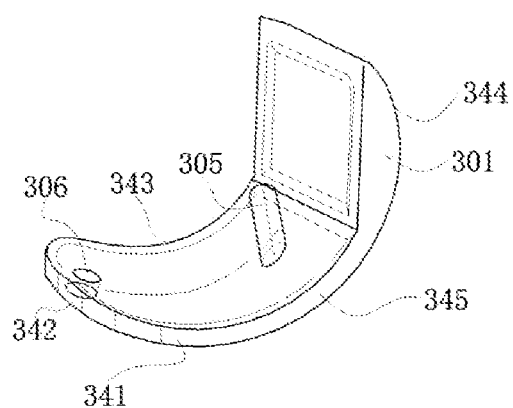
FIG. 17 is stereogram illustrating an UKA prosthesis of a lateral femoral condyle according to an embodiment of the present disclosure.

From the perspective of an axial section, the articular surface of the UKA prosthesis 301 of the lateral femoral condyle is asymmetrical, as shown in FIG. 12. The prosthesis is placed to be parallel to the Whiteside line and perpendicular to the TEA. There are straight edges 343, 345 on medial and lateral condyles of the prosthesis respectively, and the straight edges are parallel to the Whiteside line and perpendicular to the TEA. The lateral arc edge 341 is arc-shaped to adapt to a shape of a distal shape of the lateral femoral condyle; an anterior arc edge 342 has a curvature corresponding to curvature parameters of the circle 321, and a posterior portion 344 has a curvature of the ellipse 96 in the coronal section. Therefore, a stereogram of the UKA prosthesis 301 of the lateral femoral condyle is shown in FIG. 17. In addition to various positions described above, the inside sides of the prosthesis have corresponding concave grooves to adapt to the bone cement.

Operation steps of placing the UKA prosthesis of the lateral femoral condyle are the same as steps for placing the UKA prosthesis of the medial condyle, and there is a corresponding abrasive tool having a special shape, which will not be described again.

Figure 18:
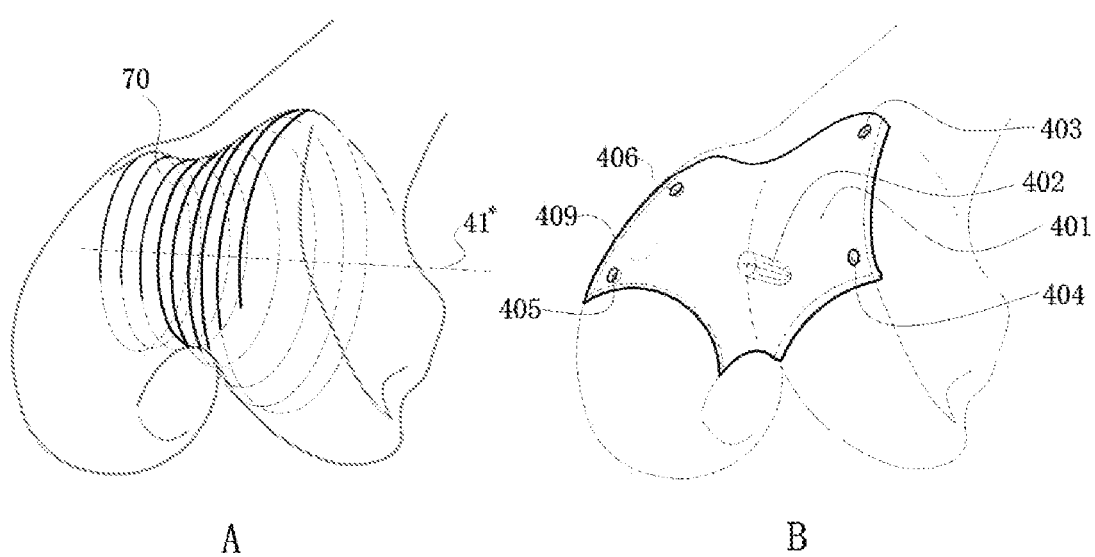
FIG. 18 is a construction principle and a stereogram of an UKA prosthesis of a femoral trochlea according to an embodiment of the present disclosure.

The UKA prosthesis of the femoral trochlea according to the embodiments of the present disclosure has a geometry of an ellipse or a circle of the medial trochlea and a geometry of a circle or an ellipse of a lateral trochlea in the sagittal section, and designs adapted to non-patella arthroplasty and patella arthroplasty. For example, the femoral trochlea prosthesis 401 comprises an articular surface, which is a surface in contact with an articular surface of a patella during motion of a knee joint, wherein the articular surface appears in a sagittal section as a set of an arc (37) of a ellipse or circle 40 and an arc 77 of a ellipse or circle 80; and an inside side which is a portion adjacent to an osteotomy surface of a femoral trochlear portion and a bone cement after the prosthesis is placed, wherein the surface appears as an inside side 409 conformal to an articular surface of the femoral trochlea. According to the above embodiment, the medial and lateral femoral trochleas are formed by arranging the arcs of ellipses and the arcs of circles concentrically respectively, as shown in FIG. 4. Therefore, the UKA prosthesis 401 of the femoral trochlea according to the present disclosure is designed to be formed by a geometry of ellipses of the medial femoral trochlea and circles of the lateral femoral trochlea, which are arranged concentrically. A concentric axis 41* connecting the centers of 41, 41', and 41") is spatially parallel to the TEA and perpendicular to the Whiteside line. As shown in FIG. 18A, illustrated is the medial and lateral trochlear portions being formed of concentric ellipses and circles, and a central circle 70 is a circle at the most concave portion of the trochlea which passes through the Whiteside line. The UKA prosthesis 401 of the femoral trochlea has a pillar 402 at a center of inside structure thereof and four surrounding locking screw holes 403, 404, 405, 406 in which locking screws are mounted, as shown in FIG. 18B.

In the above embodiments, the UKA prosthesis of the lateral femoral condyle is designed based on the elliptical structure of the lateral femoral condyle, and the ellipse of the lateral femoral condyle is designed according to a shape of an articular cartilage surface of a lateral femoral condyle of a knee joint of a normal human body. The ellipse of the lateral femoral condyle is slightly less than the ellipse of the medial femoral condyle. A major axis direction of the lateral femoral condyle is rotated clockwise by a certain angle relative to the ellipse of the medial femoral condyle. At the same time, centers of the ellipses of the medial and lateral femoral condyles coincide in the sagittal section of the femoral prosthesis. In an alternative solution, the ellipse of the lateral femoral condyle may be simplified to have the same major and minor axis directions as those of the ellipse of the medial femoral condyle, and the clockwise rotation step may be omitted, which further simplifies the design and manufacturing process of the femoral prosthesis. Although the shape after the change is not coincident with a shape of an articular cartilage surface of a lateral femoral condyle of a knee joint of a normal human body, it is also feasible. A good joint kinematic effect can also be obtained with a matching polyethylene tray at the tibial side.

In addition, in the design of the UKA prosthesis of the femoral trochlea, the medial and lateral femoral trochleas are described as being composed of ellipses and circles. This plan is obtained by a final statistical analysis. Although the medial femoral condyle according to most of the embodiments appears as ellipses, there are a few embodiments in which the medial femoral condyle appears as circles; and although the lateral femoral condyle according to most of the embodiments appears as circles, there are a few embodiments in which the lateral femoral condyle appears as ellipses. A specific implementation is based on an analysis on a normal knee joint morphology of Chinese people, and does not exclude differences caused by ethnic differences. If the medial femoral condyle is described as a circle, the lateral femoral condyle is described as an ellipse, or both the medial and lateral femoral condyles are described as circles, or both the medial and lateral femoral condyles are described as ellipses, a good joint kinematic effect can also be obtained with a matching patellar prosthesis.

It should be stated that the prosthesis according to the present disclosure will also be protected by the present patent in non-mass production, such as customized individualized three-dimensional (3D) printed knee joint prosthesis.

Thus, the elliptical or circular prostheses according to the embodiments of the present disclosure are more in conformity with the geometrical structure of the normal human knee joint. This ellipse and circle principle simplifies the complex, un-interpretable knee joint structure into a simple and effectively repeatable elliptical and circular shapes.

In addition, for the femoral prosthesis consisting of ellipse and circle principle according to the embodiments of the present disclosure, parameters of various components thereof may be represented by ellipses, circles, and important angle parameters, and change accordingly with various parameters, to achieve precise production of different prosthetic sizes. Further, each individual UKA prosthesis can be used alone or in combination. Correction of articular alignment can be achieved.

Although the present disclosure has been described with reference to a few exemplary embodiments, it is understood that the terms used are illustrative and exemplary and not restrictive. The present disclosure may be embodied in a variety of forms without departing from the spirit or scope of the present disclosure, and it is to be understood that the above-described embodiments are not limited to the details described above, and should be widely explained within the spirit and scope defined by the appended claims. Therefore, all changes and modifications which come within the scope of the claims or the equivalents thereof are intended to be covered by the appended claims.

I claim:

1. An artificial femoral prosthesis for knee arthroplasty, comprising:
    medial members, comprising a medial condyle portion and a medial trochlear portion, wherein an articular surface of the medial condyle portion appears in a sagittal section as an arc of a first ellipse, and an articular surface of the medial trochlear portion appears in the sagittal section as an arc of a second ellipse; and
    lateral members, comprising a lateral trochlear portion and a lateral condyle portion, wherein an articular surface of the lateral trochlear portion appears in the sagittal section as an arc of a third ellipse, and an articular surface of the lateral condyle portion appears in the sagittal section as an arc of a fourth ellipse,
    wherein an articular surface of a most concave portion of a trochlear groove between the medial trochlear portion and the lateral trochlear portion is an arc of a fifth circle in the sagittal section.

2. The artificial femoral prosthesis according to claim 1, wherein a major axis of the first ellipse is perpendicular to a disphyseal axis of a femur, and a center of the first ellipse corresponds to an attachment point of a medial collateral ligament of the medial femoral condyle, and
    a major axis of the fourth ellipse is angled clockwise relative to a major axis of the first ellipse, and a center of the fourth ellipse corresponds to the an attachment point of a lateral collateral ligament on the lateral femoral condyle.

3. The artificial femoral prosthesis according to claim 1, wherein a center of the first ellipse and a center of the fourth ellipse coincide in the sagittal section, and a line for connecting the centers is in a direction of TransEpicondylar Axis (TEA), and is perpendicular to Whiteside line, and
    a major axis of the second ellipse is perpendicular to a major axis of the first ellipse, a center of the second ellipse and a center (41″) of the third ellipse coincide in the sagittal section, and a line for connecting the centers (41,41″) is in a direction of TransEpicondylar Axis (TEA), and is perpendicular to Whiteside line.

4. The artificial femoral prosthesis according to claim 1, wherein a major axis and a minor axis of the first ellipse intersect with a major axis and a minor axis of the second ellipse to form a rectangle having a length (107) between 8 mm and 16 mm and a width (between 4 mm and 12 mm,
    a major axis and a minor axis of the third ellipse intersect with a major axis and a minor axis of the fourth ellipse to form a rectangle having a length between 8 mm and 16 mm and a width between 4 mm and 12 mm,
    an angle between a line for connecting a center of the first ellipse and a center of the second ellipse and a major axis of the first ellipse ranges from 25 degrees to 35 degrees, and an angle between a line for connecting a center of the third ellipse and a center of the fourth ellipse and a major axis of the first ellipse ranges from 25 degrees to 35 degrees.

5. The artificial femoral prosthesis according to claim 1, wherein all centers of consecutive ellipses on sagittal planes of the medical femoral condyle are concentric corresponding to first ellipses, and major axes and minor axes of the these ellipses are in the same direction respectively, these ellipses form a shape of articular surfaces of a complete medial femoral condyle portion in a three-dimensional space, and a line for connecting all the centers coincides with TransEpicondylar Axis (TEA), and is perpendicular to Whiteside line, and
    all centers of the consecutive ellipses on sagittal planes of the lateral femoral condyle are concentric corresponding to fourth ellipses, major axes and minor axes of these ellipses are in the same direction respectively, these ellipses form a shape of articular surfaces of complete lateral femoral condyle in a three-dimensional space, and a line for connecting all the centers coincides with TransEpicondylar Axis (TEA), is perpendicular to Whiteside line, and coincides with a line for connecting centers of the ellipses of the medial femoral condyle.

6. The artificial femoral prosthesis according to claim 1, wherein all centers of consecutive ellipses on sagittal planes of the medial femoral trochlea are concentric corresponding to second ellipses, and these ellipses form a shape of articular surfaces of a complete medial femoral trochlea in a three-dimensional space, and when the articular surfaces of the medial femoral trochlea are concentric ellipses, major axes and minor axes of these ellipses are in the same direction respectively, these ellipses have different eccentricities, sizes of these ellipses are ranked in a Fibonacci sequence, and a line for connecting all the centers coincides with TransEpicondylar Axis (TEA) and is perpendicular to Whiteside line.

7. The artificial femoral prosthesis according to claim 6, wherein all centers of consecutive ellipses on sagittal planes of the lateral femoral trochlea are concentric corresponding to third ellipses, and these ellipses form a shape of articular surfaces of a complete lateral femoral trochlea in a three-dimensional space, and when the articular surfaces of the lateral femoral trochlea are concentric circles, a line for connecting all the centers coincides with TransEpicondylar Axis (TEA), is perpendicular to Whiteside line, and coincides with a line for connecting centers of the articular surfaces of the medial femoral trochlea.

8. The artificial femoral prosthesis according to claim 1, wherein a posterior portion of the lateral condyle portion is shorter than and lower than a posterior portion of the medial condyle portion in the sagittal section, and an anterior edge of the lateral trochlear portion is longer than and higher than an anterior edge of the medial trochlear portion in the sagittal section.

9. The artificial femoral prosthesis according to claim 1, wherein geometric design parameters of outer and inner surfaces of the entire femoral prosthesis are determined by a relationship and size parameters between the first ellipse and the second ellipse.

10. The artificial femoral prosthesis according to claim 1, wherein an articular surface of the medial condyle portion on a coronal plane is represented as an arc of a sixth circle in the coronal plane, which has a center coincident with a center of the first ellipse and a radius equal to a semi-minor axis of the first ellipse.

11. The artificial femoral prosthesis according to claim 10, wherein an articular surface of the lateral condyle portion on a coronal plane is represented as an arc of a seventh ellipse in the coronal plane, which has a center coincident with a center of the fourth ellipse, and an internal rotational angle of a major axis of the seventh ellipse relative to TransEpicondylar Axis (TEA) in the coronal plane ranges from 25 degrees to 35 degrees.

12. The artificial femoral prosthesis according to claim 1, wherein the articular surface of the lateral condyle portion on a coronal section is represented as an arc of a circle, which has a center coincident with a center of the fourth ellipse, and a radius equal to a semi-minor axis of the fourth ellipse.

13. The artificial femoral prosthesis according to claim 1, wherein the prosthesis is adjusted to adapt to a cruciate ligament retaining-type prosthesis or a posterior stabilizing-type prosthesis or other revision-type prostheses or an individualized 3D printed prosthesis, or a non-patella arthroplasty-type prosthesis, a patella arthroplasty-type prosthesis, or a kinematic alignment-type prosthesis or an assembly-type prosthesis.

14. The artificial femoral prosthesis according to claim 11, wherein a width of the prosthesis is directly related to size parameters of the sixth circle of the medial femoral condyle in the coronal plane and the seventh ellipse of the lateral femoral condyle in the coronal plane.

15. The artificial femoral prosthesis according to claim 14, wherein an arc of the first ellipse representing the sagittal articular surface of the medial femoral condyle in the sagittal plane has an angle ranging from 150 degrees to 200 degrees, and an arc of the fourth ellipse representing the sagittal articular surface of the lateral femoral condyle in the sagittal plane has an angle ranging from 120 degrees to 160 degrees, an arc of the sixth circle representing the coronal articular surface of the medial femoral condyle in the coronal plane has an angle ranging from 50 degrees to 90 degrees, and an arc of the seventh ellipse representing the coronal articular surface of the lateral femoral condyle in the coronal plane has an angle ranging from 50 degrees to 90 degrees.

16. A artificial tibial prosthesis for matching the artificial femoral prosthesis for knee arthroplasty according to claim 1, wherein a shape of the tibial prosthesis in a coronal plane comprises a medial tibial plateau surface and a lateral tibial plateau surface, wherein the medial tibial plateau surface has a circular concave shape adapted to a circle of a medial femoral condyle in a coronal section, and the lateral tibial plateau surface has an elliptical concave shape adapted to an ellipse of a lateral femoral condyle in the coronal section.

* * * * *